United States Patent
Claesson et al.

(10) Patent No.: US 6,774,132 B1
(45) Date of Patent: Aug. 10, 2004

(54) SPIROOXINDOLE DERIVATIVES THAT ACT AS ANALGESICS

(75) Inventors: Alf Claesson, Rönninge (SE); Britt-Marie Swahn, Södertälje (SE); Odd-Geir Berge, Rönninge (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/674,373

(22) PCT Filed: Jul. 20, 2000

(86) PCT No.: PCT/SE00/01506

§ 371 (c)(1), (2), (4) Date: Oct. 27, 2000

(87) PCT Pub. No.: WO01/05790

PCT Pub. Date: Jan. 25, 2001

(30) Foreign Application Priority Data

Jul. 21, 1999 (SE) .............................. 9902762
Jan. 27, 2000 (SE) .............................. 0000263

(51) Int. Cl.[7] ................... A61K 31/437; C07D 209/54; C07D 211/68
(52) U.S. Cl. ............................ 514/278; 546/17; 546/19
(58) Field of Search .................. 546/17, 19; 514/278

(56) References Cited

U.S. PATENT DOCUMENTS

| | | | |
|---|---|---|---|
| 3,936,459 A | 2/1976 | Kato et al. | |
| 4,632,923 A | 12/1986 | Blythin | 514/247 |
| 4,652,564 A | 3/1987 | Blythin | 514/248 |
| 5,091,387 A | 2/1992 | Evans et al. | |
| 5,376,661 A | 12/1994 | Guillaumet et al. | |
| 5,397,783 A | 3/1995 | Guillaumet et al. | |
| 5,420,150 A | 5/1995 | Guillaumet et al. | |
| 5,633,247 A | 5/1997 | Baldwin et al. | |
| 5,728,723 A | 3/1998 | Di Malta et al. | |
| 5,763,471 A | 6/1998 | Fourtillan et al. | |

FOREIGN PATENT DOCUMENTS

| | | | | |
|---|---|---|---|---|
| EP | 0 144 996 | 6/1985 | ......... | C07D/471/10 |
| WO | WO 93/15051 | 8/1993 | | |
| WO | WO 95/27712 | 10/1995 | | |
| WO | WO 97/11697 | 4/1997 | | |
| WO | WO 97/41125 | 11/1997 | | |
| WO | WO 01/05790 | 1/2001 | | |

OTHER PUBLICATIONS

Oxindole–3–spiropyrrolidines and piperidines . . . Milton Kornet et al 1976.*
Kornet et al., "Oxindole–3–spiropyrrolidines and —piperidines. Synthesis and local anesthetic activity", Journal of Medical Chemistry, 1976, vol. 19, No. 7, p. 892–898.
Grundy et al., "An elimination reaction of 0–alkoxycarbonylbenzyl bromides", Chemistry and Industry, 1956, p. 1145–1146.
Jossang et al., "Horsfiline, an oxindole alkaloid from Horsfieldia superba", J. Organ. Chemistry, vol. 56, 1991, p. 6527–6530.
Kuehne et al. "Studies in biomimetic alkaloid syntheses. 2. Synthesis of vincadifformine from tetrahydro–β–carboline through a secodine intermediate", J. Organ. Chemistry, vol. 43, No. 19, 1978, p. 3705–3710.
Pellegrini et al., "Synthesis of the oxindole alkaloid (–)–horsfiline", Tetrahedron: Assymetry vol. 5, No. 10, p. 1979–1992 1994.

* cited by examiner

Primary Examiner—Rita Desai
(74) Attorney, Agent, or Firm—Michael A. Sanzo; Fitch, Even, Tabin & Flannery

(57) ABSTRACT

The present invention relates to certain spirooxindole derivatives and to pharmaceutically acceptable salts thereof, which exhibit good analgesic properties and are effective in the treatment of chronic pain. The derivatives have the structure of formula I:

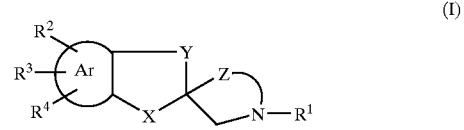

(I)

wherein:
  Ar is benzene or pyridine;
  X is NHCO—; —CONH—; or —NH—SO$_2$—;
  Y is a single bond; and
  Z is —CH═CHCH$_2$.

24 Claims, No Drawings

SPIROOXINDOLE DERIVATIVES THAT ACT AS ANALGESICS

CROSS REFERENCE TO RELATED APPLICATIONS

The present application represents U.S. national stage of international application PCT/SE00/01506, with an international filing date of Jul. 20, 2000. The international application claims priority to Swedish application 9902762-5, filed on Jul. 21, 1999 and to Swedish application 0000263-4, filed on Jan. 27, 2000.

TECHNICAL FIELD

The present invention relates to novel spirooxindole derivatives, and pharmaceutically acceptable salts thereof, with an analgesic effect. The compounds of the invention can thus be used in the prevention and treatment of pain. In further aspects, the invention relates to compounds for use in therapy; to processes for preparation of such new compounds; to pharmaceutical compositions containing at least one compound of the invention, or a pharmaceutically acceptable salt thereof, as active ingredient; and to the use of the active compounds in the manufacture of medicaments for the medical use indicated above. The invention also relates to new intermediates for use in the preparation of the novel compounds.

BACKGROUND ART

Certain spirooxindole derivatives are known as intermediates in the syntheses of vasopressin receptor ligands from U.S. Pat. No. 5,728,723 (Elf Sanofi). Patent applications WO 9741125 (SKB), WO 9711697 (MSD), WO 9527712 (CEMAF), and WO 9315051 (Elf) also discloses spirooxindoles as synthetic intermediates.

Certain spirooxindole derivatives are known as local anesthetics from Komet and Thio, *Journal of Medicinal Chemistry* 1976, 19, 892–8. This publication discloses racemic mixtures and biological studies were limited to toxicity ($LD_{50}$) in mice and local anesthetic activity (rat sciatic nerve blocking) in which test the compounds were found inferior to lidocaine. No analgesic effects of the spirooxindole derivatives are mentioned.

However, there remains a need for new therapeutic agents to treat chronic pain. Chronic pain can be caused by injury to nerves or by a variety of lesions. As of today there is no clear understanding why some, more or less visible injuries may elicit pain. Medical doctors often find even strong analgesics, such as opioids, distressfully inefficacious when the pain state is involving the nervous system itself, peripheral as well as central. These pain states are often referred to as neuropathic pain. As a final resort clinicians often prescribe drugs which are not considered true analgesics but which by trial and error have been found partly useful. Such agents include tricyclic antidepressants, for example amitriptylin, anticonvulsants like carbamazepine and gabapentin, and some local anesthetics and antiarrhythmics, especially mexiletine.

It has surprisingly been found that certain spirooxindole derivatives exhibit good analgesic properties and are particularly effective in the treatment of chronic pain.

DISCLOSURE OF THE INVENTION

It has surprisingly been found that compounds of the Formula I, which are spirooxindole derivatives, are particularly effective analgesic compounds and thereby suitable in the treatment of pain.

In one aspect, the present invention thus relates to compounds of the general Formula I

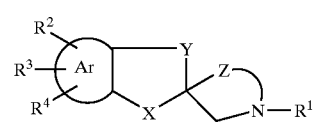

(I)

or a pharmaceutically acceptable salt thereof, wherein
$R^1$ is
  a) H,
  b) substituted or unsubstituted $C_1$–$C_6$ alkyl,
  c) $C_1$–$C_6$ alkoxy $C_2$–$C_6$ alkyl,
  d) $C_1$–$C_6$ alkylthio $C_2$–$C_6$ alkyl,
  e) halogenated $C_1$–$C_6$ alkyl,
  f) aryl $C_1$–$C_6$ alkyl,
  g) $C_1$–$C_6$ alkenyl, or
  h) $C_1$–$C_6$ cycloalkyl $C_1$–$C_2$ alkyl;
$R^2$ is
  a) H,
  b) $C_1$–$C_6$ alkyl,
  c) $C_2$–$C_4$ alkynyl,
  d) halogen,
  e) substituted or unsubstituted carbamoyl,
  f) substituted or unsubstituted carbamoyloxy,
  g) $C_1$–$C_6$ alkylcarbonyl,
  h) $C_1$–$C_6$ alkoxycarbonyl,
  i) $C_1$–$C_6$ alkylcarbonyloxy,
  j) hydroxy-substituted $C_1$–$C_6$ alkyl,
  k) cyano,
  l) nitro,
  m) amino,
  n) halogenated $C_1$–$C_6$ alkyl,
  o) halogenated $C_1$–$C_6$ alkoxy,
  p) halogenated $C_1$–$C_6$ alkylthio,
  q) $C_1$–$C_6$ alkylsulfinyl,
  r) $C_1$–$C_6$ alkylsulfonyl,
  s) $C_1$–$C_4$ alkylsulfinylalkyl,
  t) $C_1$–$C_4$ alkylsulfonylalkyl,
  u) $C_1$–$C_6$ alkylsulfonylamino,
  v) halogenated $C_1$–$C_6$ alkylsulfonylamino,
  w) halogenated $C_1$–$C_2$ alkylsulfonyloxy,
  x) aminosulfonyl,
  y) aminosulfonyloxy,
  z) aryl,
    aa) heteroaryl,
    bb) arylcarbonyl,
    cc) heteroarylcarbonyl,
    dd) arylsulfinyl,
    ee) heteroarylsulfinyl,
    ff) arylsulfonyl,
    gg) heteroarylsulfonyl, in which any aromatic moiety is optionally substituted,
    hh) $C_1$–$C_6$ alkylcarbonylamino,
    ii) $C_1$–$C_6$ alkoxycarbonylamino,
    ii) $C_1$–$C_6$ alkyl-thiocarbonyl,
    kk) $C_1$–$C_6$ alkoxy-thiocarbonyl,
    ll) formyl, or
    mm) alkoxysulfonylamino;
$R^3$ is
  a) H,
  b) $C_1$–$C_6$ alkyl,
  c) halogen,
  d) $C_1$–$C_6$ alkoxy,
  e) halogenated $C_1$–$C_4$ alkyl, f) halogenated $C_1$–$C_6$ alkoxy,
g) halogenated $C_1$–$C_6$ alkylthio,
h) $C_1$–$C_4$ alkylsulfinyl,
i) $C_1$–$C_4$ alkylsulfonyl,
j) $C_1$–$C_4$ alkylsulfinyl $C_1$–$C_6$ alkyl,
k) $C_1$–$C_4$ alkylsulfonyl $C_1$–$C_6$ alkyl,
l) $C_1$–$C_4$ alkylsulfonylamino,
m) halogenated $C_1$–$C_4$ alkylsulfonylamino,
n) aminosulfonyl, or
o) aminosulfonyloxy;

$R^4$ is
a) H,
b) $C_1$–$C_4$ alkyl, or
c) halogen;

$R^2$ and $R^3$ may together with the carbon atoms to which they are attached, form a saturated or unsaturated ring, optionally containing one or more further heteroatoms, and/or optionally substituted with one or more substituents selected from halogen, $C_1$–$C_6$ alkyl, $C_1$–$C_6$ alkoxy, $CF_3$, OH, cyano, amino, $C_1$–$C_6$alkyl-NH—, $(C_1$–$C_6$ alkyl$)_2$—N—, CN, $NH_2SO_2$, $NH_2CO$—, or $C_1$–$C_6$alkyl-CO—;

Any amino moiety in $R^2$–$R^4$ can optionally be substituted with one or two $C_1$–$C_6$ alkyl groups which may be part of a ring;

Ar is
a) benzene,
b) pyridine,
c) thiophene,
d) pyrazine,
e) pyrimidine,
f) oxazole,
g) thiazole,
h) pyrrole,
i) pyrazole, or
j) furan;

X is
a) —NHCO—,
b) —CONH—,
c) —NH—$SO_2$—,
d) —$SO_2$NH—,
e) —$OCH_2$—,
f) —$NHCH_2$—, or
g) —$NHCOCH_2$—;

Y is
a) —$CH_2$—,
b) —CH($C_1$–$C_6$alkyl)—,
c) —C($C_1$–$C_6$alkyl$)_2$—, or
d) a single bond;

Z is
a) —$CH_2CH_2CH_2$—,
b) —$CH_2CH_2CH_2CH_2$—,
c) —CH=$CHCH_2$—,
d) —CH=$CHCH_2CH_2$—, or
e) —$CH_2$CH=$CHCH_2$—;

provided that when X is —$NHCOCH_2$— then Y cannot be —$CH_2$—; and excluding the racemic compounds wherein Ar is benzene, $R^2$–$R^4$ is hydrogen, X is NHCO, Y is a single bond, Z is —$CH_2CH_2CH_2$—, and $R^1$ is ethyl or n-propyl.

The pure enantiomers, racemic mixtures and unequal mixtures of two enantiomers are within the scope of the invention. It should be understood that also all the diastereomeric forms possible are within the scope of the invention.

It will also be appreciated by those skilled in the art, although derivatives of compounds of formula I may not possess pharmacological activity as such, they may be administered parenterally or orally and thereafter metabolized in the body to form compounds of the invention which are pharmacologically active. Such derivatives, of which the N-oxide is one example, may therefore be described as "prodrugs". All prodrugs of compounds of formula I are included within the scope of the invention.

Depending on the process conditions the final products of the Formula I are obtained either in neutral or salt form. Salt forms include hydrates and other solvates and also crystalline form polymorphs. Both the free base and the salts of these end products are within the scope of the invention.

Acid addition salts of the new compounds may in a manner known per se be transformed into the free base using basic agents such as alkali or by ion exchange. The free base obtained may also form salts with organic or inorganic acids.

In the preparation of acid addition salts, preferably such acids are used which form suitably pharmaceutically acceptable salts. Examples of such acids are hydrochloric acid, sulfuric acid, phosphoric acid, nitric acid, aliphatic, alicyclic carboxylic or sulfonic acids, aromatic or heterocyclic carboxylic or sulfonic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, p-hydroxybenzoic acid, embonic acid, ethanesulfonic acid, ethanesulfonic acid, hydroxyethanesulfonic acid, alogenbensenesulfonic acid, toluenesulfonic acid or naphthalenesulfonic acid. All crystalline form polymorphs are within the scope of the invention.

Preferred compounds of the invention are those of Formula I wherein $R^1$ is
a) H,
b) $C_1$–$C_4$ alkyl,
c) $C_1$–$C_4$ alkoxy $C_1$–$C_4$ alkyl,
d) $C_1$–$C_4$ alkylthio $C_1$–$C_4$ alkyl,
e) fluorinated $C_1$–$C_4$ alkyl,
f) aryl $C_1$–$C_4$ alkyl,
g) $C_1$–$C_4$ alkenyl, or
h) cyclopropylmethyl;

$R^2$ is
a) H,
b) $C_1$–$C_4$ alkyl,
C) $C_2$–$C_3$ alkynyl,
d) halogen,
e) substituted or unsubstituted carbamoyl,
f) substituted or unsubstituted carbamoyloxy,
g) $C_1$–$C_3$ alkylcarbonyl,
h) $C_1$–$C_3$ alkoxycarbonyl,
i) $C_1$–$C_3$ alkylcarbonyloxy,
j) hydroxy-substituted $C_1$–$C_3$ alkyl,
k) cyano,
l) fluorinated $C_1$–$C_3$ alkoxy,
m) fluorinated $C_1$–$C_6$ alkylthio,
n) $C_1$–$C_3$ alkylsulfinyl,
o) $C_1$–$C_3$ alkylsulfonyl,
p) $C_1$–$C_3$ alkylsulfinyl $C_1$–$C_6$ alkyl,
q) $C_1$–$C_4$ alkylsulfonyl $C_1$–$C_6$ alkyl,
r) $C_1$–$C_3$ alkylsulfonylamino,
s) halogenated $C_1$–$C_3$ alkylsulfonylamino,
t) sulfamoyl,
u) sulfamoyloxy,
v) aryl,
w) heteroaryl,
x) heteroarylsulfinyl,
y) arylsulfonyl, z) heteroarylsulfonyl, in which any aromatic moiety is optionally substituted,
aa) $C_1$–$C_4$ alkylcarbonylamino,
bb) $C_1$–$C_3$ alkoxycarbonylamino,
cc) $C_1$–$C_3$ alkyl-thiocarbonyl, or
dd) $C_1$–$C_3$ alkoxy-thiocarbonyl;

$R^3$ is
a) H,
b) $C_1$–$C_4$ alkyl, or
c) halogen;

$R^4$ is
a) H,
b) $C_1$–$C_4$ alkyl, or
c) halogen, $R^2$ and $R^4$ may together with the carbon atoms to which they are attached, form a saturated or unsaturated ring, optionally containing one or more further heteroatoms, and/or optionally substituted with one or more substituents selected from halogen, $C_1$–$C_6$ alkyl, $C_1$–$C_6$ alkoxy, $CF_3$, OH, cyano, amino, $C_1$–$C_6$ alkyl-NH—, ($C_1$–$C_6$ alkyl)$_2$—N—, CN, $NH_2SO_2$, $NH_2CO$—, or $C_1$–$C_6$ alkyl-CO—;

Any amino moiety in $R^2$–$R^4$ can optionally be substituted with one or two $C_1$–$C_6$ alkyl groups which may be part of a ring;

Ar is
a) benzene,
b) pyridine,
c) thiophene,
d) pyrazine,
e) pyrimidine,
f) oxazole,
g) thiazole,
h) pyrrole,
i) pyrazole, or
j) furan;

X is
a) —NHCO—,
b) —CONH—,
c) —NH—$SO_2$—, or
d) —$SO_2$NH—;

Y is
a) —$CH_2$—,
b) —CH($C_1$–$C_6$alkyl)—,
c) —C($C_1$–$C_6$alkyl)$_2$— or
d) a single bond;

Z is
a) —$CH_2CH_2CH_2$—,
b) —$CH_2CH_2CH_2CH_2$—,
c) —CH=$CHCH_2$—,
d) —CH=$CHCH_2CH_2$—, or
e) —$CH_2$CH=$CHCH_2$—;

provided that when X is —$NHCOCH_2$— then Y cannot be —$CH_2$—; and excluding the racemic compounds wherein Ar is benzene, $R^2$–$R^4$ is hydrogen, X is NHCO, Y is a single bond, Z is —$CH_2CH_2CH_2$—, and R is ethyl or n-propyl.

More preferred compounds of the invention are those of Formula I wherein $R^1$ is
a) H,
b) $C_1$–$C_4$ alkyl, or
c) $C_1$–$C_4$ alkoxy $C_1$–$C_4$ alkyl;

$R^2$ is
a) H,
b) $C_1$–$C_4$ alkyl,
c) halogen,
d) substituted or unsubstituted carbamoyl,
e) substituted or unsubstituted carbamoyloxy,
f) $C_1$–$C_2$ alkylcarbonyl,
g) $C_1$–$C_3$ alkoxycarbonyl,
h) cyano,
i) fluorinated $C_1$–$C_2$ alkoxy,
j) fluorinated $C_1$–$C_6$ alkylthio,
k) $C_1$–$C_3$ alkylsulfinyl,
l) $C_1$–$C_3$ alkylsulfonyl,
m) $C_1$–$C_2$ alkylsulfonylamino,
n) $C_1$–$C_3$ alkylcarbonylamino, or
o) $C_1$–$C_3$ alkoxycarbonylamino;

$R^3$ is
a) H,
b) $C_1$–$C_4$ alkyl, or
c) halogen;

$R^4$ is
a) H,
b) $C_1$–$C_4$ alkyl, or
c) halogen;

$R^2$ and $R^3$ may together with the carbon atoms to which they are attached, form a saturated or unsaturated ring, optionally containing one or more further heteroatoms, and/or optionally substituted with one or more substituents selected from halogen, $C_1$–$C_6$ alkyl, $C_1$–$C_6$ alkoxy, $CF_3$, OH, cyano, amino, $C_1$–$C_6$ alkyl-NH—, ($C_1$–$C_6$ alkyl)$_2$—N—, CN, $NH_2SO_2$, $NH_2CO$—, or $C_1$–$C_6$ alkyl-CO—;

Any amino moiety in $R^2$–$R^4$ can optionally be substituted with one or two $C_1$–$C_6$ alkyl groups which may be part of a ring;

Ar is
a) benzene,
b) pyridine,
c) thiophene,
d) pyrazine,
e) pyrimidine,
f) oxazole,
g) thiazole,
h) pyrrole,
i) pyrazole, or
j) furan;

X is
a) —NHCO—,
b) —CONH—,
c) —NH—$SO_2$—, or
d) —$SO_2$NH—;

Y is
a) —$CH_2$—,
b) —CH($C_1$–$C_6$ alkyl)—,
c) —C($C_1$–$C_6$alkyl)$_2$—, or
d) a single bond;

Z is
a) —$CH_2CH_2CH_2$—,
b) —$CH_2CH_2CH_2CH_2$—,
c) —CH=$CHCH_2$—,
d) —$CH_2CHCH_2CH_2$—, or
e) —$CH_2$CH=$CHCH_2$—;

including the racemic compounds wherein Ar is benzene, $R^2$–$R^4$ is hydrogen, X is NHCO, Y is a single bond, Z is —$CH_2CH_2CH_2$—, and R is ethyl or n-propyl.

Particularly preferred compounds of the invention are those of Formula I wherein $R^1$ is H;

$R^2$ is
a) H,
b) $C_1$–$C_4$ alkyl, or
c) halogen;

$R^3$ is
a) H,
b) $C_1$–$C_4$ alkyl, or
c) halogen;

$R^4$ is
a) H,
b) $C_1$–$C_4$ alkyl, or
c) halogen;

Ar is
a) benzene, or
b) pyridine;

X is
a) —NHCO—,
b) —CONH—, or
c) —NH—SO 2—;

Y is a single bond;

Z is
a) $CH_2CH_2CH_2$—, or
b) —CH=$CHCH_2$—, excluding the racemic compounds wherein Ar is benzene, $R^2$–$R^4$ is hydrogen, X is NHCO, is a single bond, Z is —$CH_2CH_2CH_2$—, and $R^1$ is ethyl or n-propyl.

It has furthermore surprisingly been found that the (S)-enantiomers of the compounds of formula I possess a higher analgesic activity than the (R)-enantiomers and are thus preferred for therapeutic use before the latter and the racemic mixtures.

Another aspect of the present invention is therefore the S-enantiomer, referring to the marked spirocarbon, of the compounds of the general Formula I

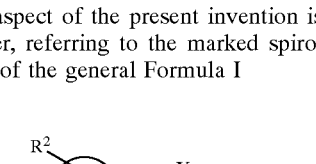

(I)

or a pharmaceutically acceptable salt thereof, as defined above.

The following definitions shall apply throughout the specification and the appended claims:

The term "$C_1$–$C_6$ alkyl" denotes a cyclic or linear, straight or branched, substituted or unsubstituted alkyl group having from 1 to 6 carbon atoms. Examples of said alkyl include, but is not limited to methyl, ethyl, n-propyl, iso-propyl, n-butyl, iso-butyl, sec-butyl, clohexyl, and cyclopentyl.

The term "$C_1$–$C_6$ alkoxy" denotes a group O-alkyl, wherein alkyl is as defined above.

The terms "$C_1$–$C_4$ alkyl", "$C_1$–$C_3$ alkyl", "$C_1$–$C_2$ alkyl" have the corresponding meaning as "$C_1$–$C_6$ alkyl".

The term "halogen" includes fluoro, chloro, bromo and iodo groups.

The term "aryl" denotes a substituted or unsubstituted $C_6$–$C_{14}$ aromatic hydrocarbon and includes, but is not limited to, benzene, naphtalene, indene, antracene, fenantrene, and fluorene.

The term "substituted" denotes e.g. an $C_1$–$C_6$ alkyl, $C_1$–$C_6$ alkylaryl or aryl group as defined above which is substituted by one or more alkyl, alkoxy, halogen, amino, thiol, nitro, hydroxy, acyl, cyano or oxo groups.

The term "heteroatoms" denotes a nitrogen, oxygen, sulfur, or a phosphorous atom.

Most preferred compounds according to the invention are listed in the following table. The compounds can be in neutral form or in salt form as earlier indicated, for example in hydrochloride form.

5-Fluorospiro[indolin-3,3'-piperidin]-2-one
5-Fluoro-1'-isopropylspiro[indolin-3,3'-piperidin]-2-one
(R)-5-Fluoro-1'-isopropylspiro[indolin-3,3'-piperidin]-2-one
(S)-5-Fluoro-1'-isopropylspiro[indolin-3,3'-piperidin]-2-one
5,7-Difluorospiro[indolin-3,3'-piperidin]-2-one acetate
5,7-Difluoro-1'-isopropylspiro[indolin-3,3'-piperidin]-2-one
(S)-5,7-Difluoro-1'-isopropylspiro[indolin-3,3'-piperidin]-2-one
5-Dimethylspiro[indolin-3,3'-piperidin]-2-one
5-Methyl-1'-isopropyl-spiro[indolin-3,3'-piperidin]-2-one
6-Methyl-1'isopropyl-spiro[indolin-3,3'-piperidin]-2-one
4-Methylspiro[indolin-3,3'-piperidin]-2-one
4-Methyl-1'-isopropylspiro[indolin-3,3'-piperidin]-2-one
4-Methyl-1'-propylspiro[indolin-3,3'-piperidin]-2-one
7-Fluorospiro[indolin-3,3'-(1,2,3,6-tetrahydropyridin)]-2-one
(S)-(+)-7-Fluorospiro[indolin-3,3'-piperidin]-2-one
Spiro[indolin-3,3'-piperidin]-2-one
1'-Ethylspiro[indolin-3,3'-piperidin]-2-one
1'-Propyl-spiro[indolin-3,3'-piperidin]-2-one
1'-Isopropylspiro[indolin-3,3'-piperidin]-2-one
1'-Allylspiro[indolin-3,3'-piperidin]-2-one
1'-Cyclopropylmethylspiro[indolin-3,3'-piperidin]-2-one
1'-Butylspiro[indolin-3,3'-piperidin]-2-one
1'-s-Butylspiro[indolin-3,3'-piperidin]-2-one
(S)-(+)-1'-Propylspiro[indolin-3,3'-piperidin]-2-one
1'-Propylspiro[4-azaindolin-3,3'-piperidin]-2-one
1'-Butylspiro[4-azaindolin-3,3'-piperidin]-2-one
1'-sec-Butylspiro[4-aza-indolin-3,3 '-piperidin]-2-one
1'-Propyl-5-chlorospiro[7-aza-indolin-3,3'-piperidin]-2-one
1'-Propylspiro[7-azaindolin-3,3'-piperidin]-2-one
1'-Propyl-6-methylspiro[7-aza indolin-3,3'-piperidin]-2-one
1'-Propylspiro[isoindolin-3,3'-piperidin]-1-one Hydrochloride
1'-Isopropylspiro[indoline-3,3'-piperidine]hydrochloride
2,3-Dihydro-1H-1'-Propylspiro[thieno[3,2-b]pyrrol-3,3'-piperidin]-2-one
2,3,1',2',3',6'-Hexahydro-1H-spiro[thieno[3,2-b]pyrrol-3,3'-pyridin]-2-one
2,3,1',2',3',6'-Hexahydro-1H-spiro[5,8-diazaindol-3,3'-pyridin]-2-one
1',2',3'4'-Tetrahydrospiro[indolin-3,3 '-(7H)-azepin]-2-one
1',2',3'4'-Tetrahydrospiro[7-azaindolin-3,3'-(7H)-azepin)-2-one
1'-Ethyl-1',2',3'4'-tetrahydrospiro[4-azaindolin-3,3'-(7H)-azepin)-2-one
1'-Propylspiro[indolin-3,3'-piperidin]-2-one 1'-oxide Further Most Preferred Compounds According to the Invention Also these compounds can be in neutral form or in salt form as earlier indicated.

(S)-5-Chloro-7-fluorospiro[indolin-3,3'-(1,2,3,6-tetrahydropyridin)]-2-one (S)-5-Methylspiro[7-azaindoline-3,3'-(1,2,3,6-tetrahydropyridin)]-2-one (S)-5,6-Dimethylspiro[7-azaindoline-3,3'-(1,2,3,6-tetrahydropyridin)]-2-one (S)-6-Methylspiro[7-azaindoline-3,3'-(1,2,3,6-tetrahydropyridin)]-2-one (S)-5-Chlorospiro[7-azaindoline-3,3'-(1,2,3,6-tetrahydropyridin)]-2-one (S)-5,7-Difluorospiro[indoline-3,3'-(1,2,3,6-tetrahydropyridin)]-2-one (S)-7-Chlorospiro[indoline-3,3'-(1,2,3,6-tetrahydropyridin)]-2-one (S)-7-Fluoro-5-methylspiro[indoline-3,3'-(1,2,3,6-tetrahydropyridin)]-2-one (S)-5-Methoxyspiro[indoline-3,3'-(1,2,3,6-tetrahydropyridin)]-2-one (S)-5-Chlorospiro[indoline-3,3'-piperidin]-2-one

PREPARATION

The present invention also provides the following processes for the preparation of compounds of the general Formula I. The compounds of the present invention can be prepared by methods known in the art using commercially available, or readily prepared, starting materials. Many useful methods for synthesis of oxindoles are reviewed by G. M. Karp in *Org. Prep. Proced. Int.* 1993, 25, 481–513, which is incorporated herein by reference.

It is to be understood that certain functional groups may interfere with other reactants or reagents under the reaction conditions and therefore may need temporary protection. The use of protecting groups is described in 'Protective Groups in Organic Synthesis', 2nd edition, T. W. Greene & P. G. M. Wutz, Wiley-Interscience (1991).

Process A

A process for manufacture of compounds with the general Formula I comprises the following steps:

a) Compounds of Formula IV

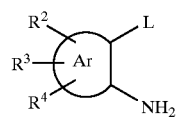

IV wherein L is a halogen or a trifluoromethylsulfonyloxy group, Ar, $R^2$–$R^4$ are as defined in Formula I, or can be converted into such groups later in the synthesis sequence, is coupled with a compound of the general Formula II, or a corresponding lower alkyl ester, e.g methyl or ethyl ester,

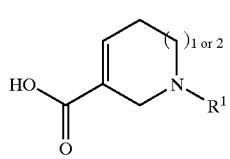

II wherein $R^1$ is as defined for Formula I or is a nitrogen protecting group, e.g. a Boc group, to give a compound of the general Formula VII

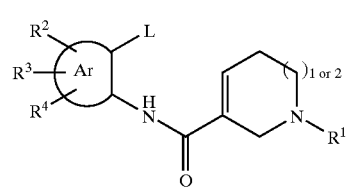

VII b) The resulting amide of the general Formula VII is then cyclized using Heck reaction conditions with palladium as a catalyst or sometimes under radical generating conditions to give, after optional removal of protecting groups, a compound of the general formula I When the above formed spiro compound contains a double bond this may be hydrogenated over a metal catalyst to give the corresponding saturated compound, or by other methods well known to those skilled in the art. The product is thereafter deprotected, if necessary, or the cyclized protected intermediate compound may be further reacted with, for example organometallic reagents, to give new compounds of the invention in which an alkyl or alkynyl group is substituted for a bromine or an aryl- or alkylsulfonyloxy group.

Process B a) Compound of Formula IV

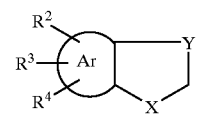

IV wherein Ar, $R^2$–$R^4$, Y are as defined in Formula I, and X is —NHCO— or —NH—$SO_2$ are alkylated with a compound of the general Formula IX

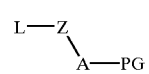

IX wherein Z is as defined in Formula I, L is a bromine, iodine, aryl or alkylsulfonyloxy group, e.g. trifluoromethylsulfonyloxy group, A is oxygen or nitrogen, and PG is a suitable protecting group or, when A is nitrogen, equals $R^1$ of Formula I, to give compounds of the general formula XII

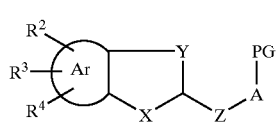

XII wherein Ar, $R^2$–$R^4$, Y, and Z are as defined in Formula I, X is —NHCO—, or —NH—$SO_2$—, A is oxygen or nitrogen and PG is a suitable protecting group or, when A is nitrogen, equals $R^1$ of Formula I.

b) An optional transformation step is performed when A is oxygen, wherein the oxygen function is converted into the corresponding amino function by methods well known in the art. One suitable way of accomplishing this conversion is to remove the protecting group to generate the corresponding primary alcohol, which is thereafter converted into a suitable leaving groups, e.g. a tosylate group. The leaving group is thereafter displaced by a suitable amino nucleophile to give a compound of the general formula XII, wherein A is nitrogen.

c) Compounds of the general formula XII can thereafter and after optional removal of protecting groups be cyclized to the Spiro system to give compounds of the formula I under standard Mannich conditions.

Process C a) Compounds of the general Formula III

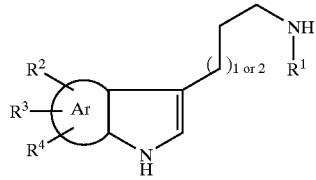

wherein Ar, $R^1$–$R^4$ are as defined in Formula I or $R^1$ is a benzylic protecting group, are oxidised into compounds of the general Formula VI,

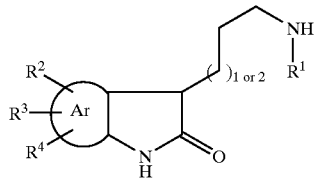

wherein Ar, $R^1$–$R^4$ are as defined in Formula I or $R^1$ is a benzylic protecting group, as is described in Kornet and Thio, *Journal of Medicinal Chemistry* 1976, 19, 892–8 or as referred to in the previously mentioned review by Karp.

c) Compounds of the general Formula VI are thereafter cyclized under standard Mannich reaction conditions to give a compound of the general Formula I.

Process D a) Compounds of the general Formula V

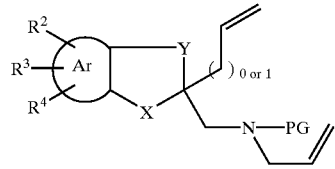

wherein Ar, $R^2$–$R^4$, X and Y are as defined in Formula I and PG is an amino protecting group, is ring-closed using a ruthenium or molybdene complex as a catalyst under standard reaction conditions to give compounds of the general formula VIII

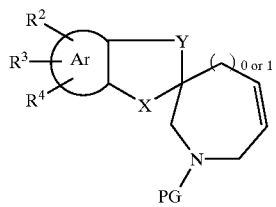

This metathesis reaction is described in more detail in the review by Grubbs, R. H. and Chang, S. *Tetrahedron* 1998, 54, 4413–50.

The intermediate V may be prepared by methods known to the one skilled in the art, for example by alkylation of the intermediate IV with e.g. allyl bromide followed by a Mannich reaction with a secondary amine to give a compound of the general formula Va, as is schematically shown below.

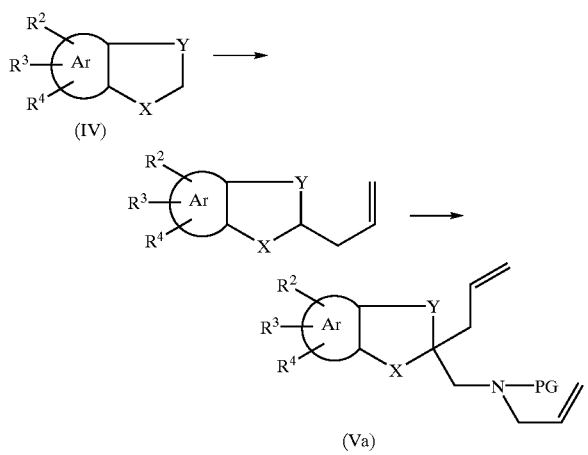

In process B and C the amino protecting group used is preferably an easily removable group, for example groups belonging to the arylmethyl class which can be readily removed by hydrogenolysis, thus releasing the secondary amine of formula I ($R^1$=H). Said compound can be converted to a tertiary amine, by alkylating methods well known in the art. Other suitable protective groups that are described in the organic chemical literature is, for example, an allyl carbamate or a 4-methoxybenzyl group.

Many interconversions of the $R^2$ and $R^3$ groups are also evident to one skilled in the art.

Compounds of the general formula I prepared in this way are racemic. As is well known in the art resolution of the two enantiomers can be conveniently achieved by classical crystallization methods by using a chiral acid such as L- or D-ditoluoyltartaric acid or (+) or (−)-1-camphorsulfonic acid in a suitable solvent such as acetone, water, alcohol, ethyl acetate or their mixture. Another method to achieve the same goal is to separate the enantiomers by chromatography on a chiral column such as Chiralcel OD or Kromasil TBB which are commercially available. A further well known means to obtain pure enantiomers is by preparing a derivative of a racemic intermediate, for example an amide of a secondary amine, with an enantiomerically pure acid and then separating the so formed diastereomers by crystallization or by chromatography.

MEDICAL USE

In a further aspect, the present invention relates to compounds of the formula I for use in therapy, in particular for use in the treatment of pain. The invention also provides the use of a compound of the formula I in the manufacture of a medicament for the treatment of pain.

The novel compounds of the present invention are useful in therapy, especially for the treatment and/or prophylaxis of pain of widely different origins and causes and include acute as well as chronic pain states. Examples are pain caused by chemical, mechanical, radiation, thermal, infectious or inflammatory tissue trauma or cancer, postoperative pain, headache and migraine, various arthritic and inflammatory conditions such as osteo and rheumatoid arthritis, myofascial and low back pain.

Also neuropathic conditions of central or peripheral origin can be treated or prevented with the compounds of the invention. Examples of these pain conditions are trigeminal neuralgia, postherpetic neuralgia (PHN), diabetic mono/poly neuropathy, nerve trauma, spinal cord injury, central post stroke, multiple sclerosis and Parkinson's disease. Other pain states of visceral origin such as caused by ulcer, dysmenorrhea, endometriosis, IBS, dyspepsia etc. can also be treated or prevented with the compounds of the invention. The compounds of the invention are useful as therapeutic agents in disease states with inappropriate neuronal activity or in neuroprotection for example as anticonvulsants in epilepsy, in the treatment of itch, tinnitus, Parkinson's disease, multiple sclerosis, amyotrophic lateral sclerosis (ALS), Alzheimer, stroke, cerebral ischaemia, traumatic brain injury, Huntingdon's chorea, schizophrenia, obsessive compulsive disorders (OCD), neurological deficits associated with AIDS, sleep disorders (including circadian rhythm disorders, insomnia & narcolepsy), tics (e.g. Tourette's syndrome), and muscular rigidity (spasticity).

A primary aim of the invention is to use compounds of the formula I for oral treatment of neuropathic or central pain states.

The compounds of the invention are also useful for treatment of effects associated with withdrawal from substances of abuse such as cocaine, nicotine, alcohol and benzodiazepines.

In a further aspect the invention provides the use of a compound of formula I, or a pharmaceutically acceptable salt or solvate, thereof as a therapeutic agent, in particular for the treatment and/or prophylaxis of anxiety, mania, depression, panic disorders and/or aggression.

The typical daily dose of the active substance varies within a wide range and will depend on various factors such as for example the individual requirement of each patient, the route of administration and the disease. In general, the dosages will be in the range of 0.1 to 1000 mg per day of active substance.

PHARMACEUTICAL FORMULATIONS

In yet a further aspect, the invention relates to pharmaceutical compositions containing at least one compound of the present invention, or a pharmaceutically acceptable salt thereof, as active ingredient.

For clinical use, the compounds of the invention are formulated into pharmaceutical formulations for oral, intravenous, subcutaneous, tracheal, bronchial, intranasal, pulmonary, transdermal, buccal, rectal, parenteral or other mode of administration. The pharmaceutical formulation contains a compound of the invention in combination with one or more pharmaceutically acceptable ingredients. The carrier may be in the form of a solid, semi-solid or liquid diluent, or a capsule. These pharmaceutical preparations are a further object of the invention. Usually the amount of active compounds is between 0.1–95% by weight of the preparation.

In the preparation of pharmaceutical formulations containing a compound of the present invention the compound selected may be mixed with solid, powdered ingredients, such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture may then be processed into granules or pressed into tablets.

Soft gelatine capsules may be prepared with capsules containing a mixture of the active compound or compounds of the invention, vegetable oil, fat, or other suitable vehicle for soft gelatine capsules. Hard gelatine capsules may contain granules of the active compound. Hard gelatine capsules may also contain the active compound in combination with solid powdered ingredients such as lactose, saccharose, sorbitol, mannitol, potato starch, cornstarch, amylopectin, cellulose derivatives or gelatine.

Dosage units for rectal administration may be prepared (i) in the form of suppositories which contain the active substance mixed with a neutral fat base; (ii) in the form of a gelatine rectal capsule which contains the active substance in a mixture with a vegetable oil, paraffin oil or other suitable vehicle for gelatine rectal capsules; (iii) in the form of a ready-made micro enema; or (iv) in the form of a dry micro enema formulation to be reconstituted in a suitable solvent just prior to administration.

Liquid preparations may be prepared in the form of syrups or suspensions, e.g. solutions or suspensions containing the active ingredient and the remainder consisting, for example, of sugar or sugar alcohols and a mixture of ethanol, water, glycerol, propylene glycol and polyethylene glycol. If desired, such liquid preparations may contain coloring agents, flavouring agents, preservatives, saccharine and carboxymethyl cellulose or other thickening agents. Liquid preparations may also be prepared in the form of a dry powder to be reconstituted with a suitable solvent prior to use.

Solutions for parenteral administration may be prepared as a solution of a compound of the invention in a pharmaceutically acceptable solvent. These solutions may also contain stabilizing ingredients, preservatives and/or buffering ingredients. Solutions for parenteral administration may also be prepared as a dry preparation to be reconstituted with a suitable to solvent before use.

The typical daily dose of the active substance varies within a wide range and will depend on various factors such as for example the individual requirement of each patient, the route of administration and the disease. In general, oral and parenteral dosages will be in the range of 0.1 to 1000 mg per day of active substance.

The compounds according to the present invention can also be used in formulations, together or in combination for simultaneous, separate or sequential use, with other active ingredients, such as a) opioid analgesics, for example morphine, ketobemidone or fentanyl b) analgesics of the NSAED class, for example ibuprofene, selecoxib or acetylsalicylic acid c) amino acids such as gabapentin or pregabalin d) analgesic adjuvants such as amitriptyline or mexiletine e) NMDA antagonists for example ketamine or dextrometorfan f) sodium channel blocking agents for example lidocaine g) anticonvulsants, for example carbamazepine or lamotrigine h) cannabinoids

INTERMEDIATES

A further aspect of the invention is new intermediate compounds which are useful in the synthesis of compounds according to the invention.

Thus, the invention includes (a) a compound of the formula XI

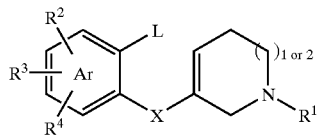

XI wherein Ar, $R^1$–$R^4$ and X are as defined for Formula I, L is bromide, iodide, or triflate and $R^1$ may also be a nitrogen protecting group, such as a alkoxycarbonyl or a benzyl group, of which t-butoxycarbonyl is especially preferred and X, when containing, a nitrogen atom, may optionally be substituted with a t-butoxycarbonyl group.

EXAMPLES

1. PREPARATION OF COMPOUNDS OF THE INVENTION

All chemicals and reagents were used as received from suppliers. $^{13}$C and $^1$H nuclear magnetic resonance (NMR) spectra were recorded on a Varian Unity 400 (400 MHz) spectrometer. Silica gel chromatography (SGC) was carried out on silica gel 60 (230–400 mesh). Mass spectrometry (MS) was carried out in the positive thermospray (TSP+), chemical ionization (CI), or in the electron impact (EI) modes.

Other abbreviations: Boc, t-butyloxycarbonyl; DCM, dichloromethane; EtOAc, ethyl acetate.

Example 1

5-Fluorospiro[indoline-3,3'-piperidin]-2-one Hydrochloride

STEP A. t-Butyl 3-(2-bromo-4-fluorophenylcarbamoyl)-1,2,5,6-tetrahydropyridine-1-carboxylate. 2-Bromo-4-fluoroaniline (2.53 g, 13.3 mmol) was dissolved in dichloromethane (30 mL) under $N_2$-atmosphere and trimethylaluminium (2.0 M in hexanes, 8 mL) was added. The solution was stirred during 15 minutes, whereupon a solution of 5,6-dihydro-2H-pyridine-1,3-dicarboxylic acid 1-t-butyl ester 3-methyl ester (3.67 g, 13.3 mmol) in DCM (20 mL) was added. The mixture was refluxed overnight and saturated $NaHCO_3$ was carefully added followed by DCM. The aqueous phase was extracted with DCM. The crude product was purified by chromatography on silica gel using a gradient of toluene to acetonitrile to give the title compound (4.55 g) in 86% yield as an yellow oil. $R^f$ 0.54 (toluene/acetonitrile 3:1). MS(TSP+) m/z calcd for $[M+NH_4]^+$: 416, 418, observed: 416, 418.

STEP B. t-Butyl 3-[(2-bromo-4-fluorophenyl)-(t-butoxycarbonyl)-carbamoyl]-1,2,5,6-tetrahydropyridine-1-carboxylate. The product from STEP A (3.51 g) was dissolved in dry acetonitrile under $N_2$-atmosphere. 4-Dimethylaminopyridine (120 mg, 0.98 mmol) and di-t-butyl dicarbonate (2.08 g, 9.53 mmol) were added. After reaction overnight the acetonitrile was stripped off and the residue was dissolved in diethyl ether (200 mL). The ethereal phase was extracted with 0.2 M aqueous solution of citric acid (3×50 mL) and then with saturated $NaHCO_3$ (3×50 mL). The product was purified by chromatography on silica gel using a gradient of toluene to acetonitrile to give the title compound in 91% yield as a yellow oil. MS(TSP+) m/z observed: 516, 518 (20%).

STEP C. Di-t-butyl 5-fluoro-2-oxospiro[indoline-3,31-(1,2,3,6-tetrahydropyridin)]-1,1'-dicarboxylate. The amide from STEP B (994 mg, 1.99 mmol) was dissolved in acetonitrile (20 mL) under $N_2$-atmosphere. Triphenylphosphine (133 mg, 0.51 mmol), triethylamine (0.42 mL, 3 mmol) and palladium acetate (50 mg, 0.22 mmol) were added. The mixture was refluxed for 5 days under $N_2$-atmosphere. The crude product was purified by chromatography on silica gel and eluted with a gradient of toluene to acetonitrile to give the title compound (604 mg) in 73% yield as a yellow oil. $R^f$ 0.58 (toluene/acetonitrile 3:1). MS(CI, $NH_3$) m/z 436.

STEP D. t-Butyl 5-fluoro-2-oxospiro[indoline-3,3'-(1,2,3,6-tetrahydro-pyridin)]-1'-carboxylate. The compound from STEP A (1.00 g, 2.50 mmol) was cyclised to the title compound (382 mg) in 48% yield following the same procedure as described in STEP C. MS (TSP+) m/z $[M+H]^+$: 319.

STEP E. Di-t-butyl 5-fluoro-2-oxospiro[indoline-3,3'-piperidin]-1,1'-dicarboxylate. The product from STEP C (590 mg, 1.41 mmol) was hydrogenated in absolute ethanol (20 mL) using $PtO_2$ and $H_2$ (3.5 atm) for 2 days. The reaction mixture was filtered using OOH-filter paper and the solvent was evaporated to give the title compound (563 mg) in 95% yield. MS (TSP+) m/z calcd for $[M-BOC+H]^+$: 321, observed: 321.

STEP F. t-Butyl 5-fluoro-2-oxospiro[indoline-3,3'-piperidin]-1'-carboxylate. The product from STEP D (344 mg, 1.08 mmol) was transformed to the title compound (295 mg) following the same procedure as described in STEP E. MS (TSP+) m/z $(M+H)^+$: 321.

STEP G. 5-Fluorospiro[indoline-3,3'-piperidin]-2-one Hydrochloride. The product from STEP E (563 mg, 1.34 mmol) was dissolved in methanol (10 mL) and was treated with HCl (2.5 M ethereal solution, 5 mL). The solvents were stripped off to give the product (341 mg) in 99% yield as a white solid. The same procedure was also applied to the product from STEP F. MS(TSP+) m/z calcd for $[M-Cl]^+$: 221, observed: 221.

Example 2

5-Fluoro-1'-isopropylspiro[indoline-3,3'-piperidin]-2-one Hydrochloride

The amine from EXAMPLE 1 was alkylated using PROCEDURE 1, Method A. The crude product was purified by chromatography on silica gel using a gradient of toluene to acetonitrile/triethyl amine 100:5 to give the amine in 64% yield. $^{13}$C-NMR (CDCl$_3$) δ 182.3, 158.5 (d, J 236 Hz), 136.4, 135.9, 114.4 (d, J 26 Hz), 113.4 (d, J 25 Hz), 109.8, 54.8, 53.9, 49.2, 48.9, 32.0, 21.7, 18.0, 17.6. It was converted to the title compound with HCl in ether. MS(TSP+) m/z calcd for $[M-Cl]^+$: 263, observed: 263.

Example 3

(R)-5-Fluoro-1'-isopropylspiro[indoline-3,3'-piperidin]-2-one Hydrochloride

5-Fluoro-1'-isopropyl-spiro[indoline-3,3'-piperidin]-2-one (215 mg) from EXAMPLE 2 was chromatographed on a Kromasil TBB column eluting with hexane/1-propanol/1-butanol 99:0.5:0.5. The pure stereoisomer (72 mg) was collected as the first eluting peak in 67% yield and an enantiomeric excess of 97%. $[\alpha]_{589}^{22}$ −1.18°, $[\alpha]_{365}^{22}$ −10.00° (c 1.01, $CHCl_3$). It was converted to the title compound. $[\alpha]_{589}^{22}$ −6.93° (c 1.01, MeOH).

Example 4

(S)-5-Fluoro-1'-isopropylspiro[indoline-3,3'-piperidin]-2-one 62 mg was collected from EXAMPLE 3 as the second enantiomer in 58% yield and an enantiomeric excess of 99%. $[\alpha]_{589}^{22}$ +1.05°, $[\alpha]_{326}^{22}$ +9.32° (c 1.03, $CHCl_3$). It was converted to the hydrochloride. $[\alpha]_{589}^{22}$ +6.22 (c 1.03, MeOH).

Example 5

5,7-Difluorospiro[indoline-3,3'-piperidin]-2-one Acetate

STEP A. 1-Benzyl-N-(2-bromo-4,6-difluorophenyl)-1,2,5,6-tetrahydropyridine-3-carboxamide. The title compound was prepared from 2-bromo-4,6-difluoroaniline and 1-benzyl-1,2,5,6-tetrahydropyridine-3-carboxylic acid methyl ester as described in EXAMPLE 1. $R_f$ 0.53 (toluene/acetonitrile/tri-ethyl amine 10:10:1).

STEP B. 5,7-Difluoro-1'-benzylspiro[indoline-3,3'-(1,2,3,6-tetrahydropyridin)]-2-one. The product from STEP A was cyclized as described in EXAMPLE 1.

STEP C. 5,7-Difluorospiro[indoline-3,3'-piperidin]-2-one acetate. The product from STEP B was hydrogenated in glacial acetic acid (20 mL) using 10% Pd/C and $H_2$ (3.5 atm) for 24 hours. The title compound was obtained in 86% yield as a crystalline solid. MS(TSP+) m/z calcd for $[M-AcO]^+$: 239, observed: 239.

Example 6

5,7-Difluoro-1'-isopropylspiro[indoline-3,3'-piperidin]-2-one Hydrochloride

The amine from the previous EXAMPLE was alkylated as described in EXAMPLE 2 to give the free amine of the title compound in 58% yield as a white solid. $^{13}$C-NMR ($CDCl_3$) δ 180.3, 157.9 (d, J 240 Hz), 146.0 (d, J 244 Hz), 137.8, 123.2 (d, J 1Hz), 110.3 (d, J 25 Hz), 102.6 (dd, J 21, 21 Hz), 54.9, 53.9, 49.4, 48.7, 32.1, 21.6, 18.1, 17.6. It was converted to the hydrochloride. MS(TSP+) m/z calcd for $[M-Cl]^+$: 281, observed: 281.

Example 7

(S)-5,7-Difluoro-1'-isopropylspiro[indoline-3,3'-piperidin]-2-one Hydrochloride

STEP A. Chromatography. 5,7-Difluoro-1'-isopropyl-spiro[indoline-3,3'-piperidin]-2-one (231 mg) from the preceding example was chromatographed on a Kromasil TBB column eluting with hexane/1-propanol/1-butanol 98:1:1. (R)-5,7-Difluoro-1'-isopropyl-spiro[indoline-3,3'-piperidin]-2-one (94 mg) was collected as the first enantiomer in 81% yield and an enantiomeric excess of 97.6%. −0.30° (c 1.00, $CHCl_3$). (S)-5,7-Difluoro-1'-isopropyl-spiro[indoline-3,3'-piperidin]-2-one was collected as the second peak (92 mg) in 80% yield and an enantiomeric excess of 98.4%, +0.12° (c 1.00, $CHCl_3$).

STEP B. (S)-5,7-Difluoro-1'-isopropylspiro[indoline-3,3'-piperidin]-2-one hydrochloride. The (S)-enantiomer from STEP A was converted to the hydrochloride to give the title compound as a white solid, 6.200 (c 1.00, MeOH).

Example 8

5-Dimethylspiro[indoline-3,3'-piperidin]-2-one Hydrochloride

The title compound was prepared from 2-Bromo-4-methyl-aniline and arecoline hydrobromide as described in EXAMPLE 1. MS(TSP+) m/z calcd for $[M-Cl]^+$: 231, observed: 231.

Example 9

5-Methyl-1'-isopropyl-spiro[indoline-3,3'-piperidin]-2-one Hydrochloride

The title compound was obtained from 2-bromo-4-methyl-aniline and methyl N-benzyl-1,2,3,6-tetrahydropyridin-3-carboxylate as described in EXAMPLE 1. MS(TSP+) m/z calcd for $[M-Cl]^+$: 259, observed: 259.

Example 10

6-Methyl-1'-isopropyl-spiro[indoline-3,3'-piperidin]-2-one Hydrochloride

The title compound was obtained as described in EXAMPLE 9 starting with 2-iodo-5-methyl-aniline. MS(TSP+) m/z calcd for $[M-Cl]^+$: 259, observed: 259.

Example 11

6-Trifluoromethyl-1'-isopropyl-spiro[indoline-3,3'-piperidin]-2-one Hydrochloride The title compound was obtained as described in EXAMPLE 9 starting with 3-amino-4-bromo-benzotrifluoride. MS(TSP+) m/z calcd for $[M+H]^+$: 439, 441, observed: 439, 441.

Example 12

4-Methylspiro[indoline-3,3'-piperidin]-2-one Hydrochloride

The title compound was obtained as described in EXAMPLE 9 starting with 2-Bromo-3-ethylaniline. $[M]^+$: 217, observed: 217. It was converted to the hydrochloride.

Example 13

4-Methyl-1'-isopropylspiro[indoline-3,3'-piperidin]-2-one Hydrochloride

The compound from the previous EXAMPLE was alkylated to the title compound using PROCEDURE 1, Method A. $^{13}$C-NMR ($CDCl_3$): δ 181.4, 141.0, 134.6, 130.4, 127.9, 125.2, 107.5, 61.0, 56.2, 54.1, 53.7, 48.6, 28.3, 21.2,19.9, 19.5, 11.9.

Example 14

4-Methyl-1'-propylspiro[indoline-3,3'-piperidin]-2-one Hydrochloride

The compound from EXAMPLE 12 was alkylated to the title compound. $^{13}$C-NMR of the base ($CDCl_3$): δ 181.5, 141.1, 134.7, 130.8, 127.8, 125.2, 107.5, 54.6, 50.9, 49.7, 28.6, 21.6, 19.8, 19.3, 15.9. MS(TSP+) m/z calcd for [M−Cl]+: 259, observed: 259.

Example 15

(S)-(+)-4-Methylspiro[indoline-3,3'-piperidin]-2-one Hydrochloride

The title compound was prepared by separating the N-bocylated compound from EXAMPLE 12 on a Kirasil TBB column and removing the Boc group from the collected product in 1M HCl in methanol. (M−Cl)+: 217, observed: 217.

Example 16

(S)-(+)-4-Methyl-1'-propylspiro[indoline-3,3'-piperidin]-2-one Hydrochloride The compound from the previous EXAMPLE was alkylated to the title compound using PROCEDURE 1, Method B.

Example 17

7-Fluorospiro[indoline-3,3'-(1,2,3,6-tetrahydropyridin)]-2-one Hydrochloride The title compound was prepared from 2-bromo-6-fluoroaniline following the steps described in EXAMPLE 16 but deprotecting the dibocylated unsaturated intermediate. [M−Cl]+: 219, observed: 219.

Example 18

(S)-(+)-7-Fluorospiro[indoline-3,3'-piperidin]-2-one Hydrochloride

The title compound was prepared by separating the N-bocylated precursor on a Kirasil TBB column and removing the Boc group from the collected product in 1M HCl in methanol. [M−Cl]+: 219, observed: 219.

Example 19

Spiro[indoline-3,3'-piperidin]-2-one Hydrochloride

STEP A. t-Butyl 5-(2-bromophenylcarbamoyl)-1,2,5,6-tetrahydropyridin-1-carboxylate. 2-Bromaniline was amidated to the title compound as described in EXAMPLE 1. MS(TSP+) m/z calcd for [M+NH4]+: 398, 400, observed: 398, 400.

STEP B. t-Butyl 3-[(2-bromophenyl)-(t-butoxycarbonyl)-carbamoyl]-1,2,5,6-tetrahydropyridine-1-carboxylate. The compound from STEP A was bocylated to the title compound by dissolving in DCM and add di-tert-butyldicarbonate (1.2 equiv.), triethylamine (1.2 equiv.) and dimethylaminopyridine (0.07 equiv). MS(TSP+) m/z calcd for [M+NH4]+: 498, 500, observed: 498, 500.

STEP C. Di-t-butyl 2-oxospiro[indoline-3,3'-(1,2,3,6-tetrahydropyridin)]-1,1'-dicarboxylate. Obtained according to EXAMPLE 1, STEP C.

STEP D. Di-t-butyl 2-oxospiro[indoline-3,3'-piperidin]-1,1'-dicarboxylate. Obtained according to EXAMPLE 1, STEP D.

STEP E. Spiro[indoline-3,3'-piperidin]-2-one Hydrochloride. The compound from the previous step was deprotected by dissolving in 1M HCl in methanol and stirring for 1 hour. Evaporation of solvents gave the title compound. $^{13}$C-NMR (d4-MeOH): 180.6, 140.5, 129.5, 129.2, 122.8, 122.7, 110.5, 47.4, 43.7, 30.0, 23.5, 17.4 ppm

Example 20

1'-Ethylspiro[indoline-3,3'-piperidin]-2-one

The compound was prepared according to PROCEDURE 1, Method A by reaction with spiro[indoline-3,3'-piperidin]-2-one and acetaldehyde (5 equivalents). Yield: 45 mg (26%). $^{13}$C NMR of the HCl-salt (CD3OD): δ 9.6, 19.8, 31.3, 46.3, 54.2, 54.3, 55.1, 111.5, 123.9, 124.4, 130.4, 131.3, 142.6, 182.3.

Example 21

1'-Propyl-spiro[indoline-3,3'-piperidin]-2-one Hydrochloride

The compound was prepared according to PROCEDURE 1, Method A by reaction with spiro[indoline-3,3'-piperidin]-2-one and propionaldehyde (5 equivalents). Yield 65%.

Example 22

1'-Isopropylspiro[indoline-3,3'-piperidin]-2-one

The compound was prepared according to PROCEDURE 1, Method A by reaction with spiro[indoline-3,3'-piperidin]-2-one and acetone (5 equivalents). Yield: 75%. $^{13}$C NMR (CDCl3): δ 17.6, 17.7, 21.7, 32.1, 48.6, 48.8, 54.0, 54.8, 109.6, 121.6, 126.2, 127.2, 134.8, 140.1, 182.4; MS (CI, CH4): m/z (rel. int.) 245 (M+1, 100).

Example 23

1'-Allylspiro[indoline-3,3'-piperidin]-2-one

The compound was prepared according to PROCEDURE 1, Method B by reaction of spiro[indoline-3,3'-piperidin]-2-one with allyl bromide (1.1 equivalents). $^{13}$C NMR (CDCl3): δ 21.2, 31.3, 48.4, 53.3, 58.1, 61.6, 109.5, 117.2, 121.6, 125.7, 127.4, 134.3, 135.1, 140.0, 181.6; MS (CI, CH4): m/z (rel. int.) 243 (M+1, 100).

Example 24

1'-Cyclopropylmethylspiro[indoline-3,3'-piperidin]-2-one

The compound was prepared according to PROCEDURE 1, Method A by reaction of spiro[indoline-3,3'-piperidin]-2-one with 3 equiv. of cyclopropanecarboxaldehyde. Yield: 90%. $^{13}$C NMR (CDCl3): δ 3.8, 4.0, 8.3, 21.4, 31.8, 48.6, 53.3, 58.4, 63.6, 109.7, 121.7, 126.1, 127.4, 134.7, 140.0, 182.2; MS (CI, CH4): m/z (rel. int.) 257 (M+1, 100).

Example 25

1'-Butylspiro[indoline-3,3'-piperidin]-2-one

The compound was prepared according to PROCEDURE 1, Method A by reaction with spiro[indoline-3,3'-piperidin]-2-one and butyraldehyde (10 equiv.). $^{13}$C NMR (CDCl3): δ 14.1, 20.6, 21.7, 29.1, 32.0, 49.0, 53.8, 58.5, 58.9, 109.9, 121.9, 126.4, 127.6, 134.9, 140.2, 182.4; MS (TSP): m/z (rel. int.) 260/259 (M+, 25/100).

Example 26

1'-s-Butylspiro[indoline-3,3'-piperidin]-2-one

The compound was prepared according to PROCEDURE 1, Method A by reaction with spiro[indoline-3,3'-piperidin]-2-one and 2-butanone (3 equivalents). Yield: 46%. $^{13}$C NMR (CDCl$_3$): δ 11.5, 11.6, 13.3, 13.3, 21.7, 21.9, 26.4, 26.5, 32.1, 32.1, 46.1, 48.6, 49.0, 50.9, 52.4, 56.6, 61.2, 62.5, 109.6, 121.5, 121.6, 126.4, 126.5, 127.2, 134.7, 134.9, 140.1, 140.1, 182.4, 182.5; MS (CI, CH$_4$): m/z (rel. int.) 259 (M+1, 100).

Example 27

1'-Isobutylspiro[indoline-3,3'-piperidin]-2-one Hydrochloride

The compound was prepared according to PROCEDURE 1, Method A by reaction with spiro[indoline-3,3'-piperidin]-2-one and isobutyraldehyde (3 equivalents). Purification on SiO$_2$ twice (eluent: DCM/MeOH). Yield: 88 mg. $^{13}$C NMR (CD$_3$OD): δ 21.2, 21.3, 22.7, 26.7, 32.9, 50.2, 55.4, 60.4, 68.3, 110.6, 122.6, 127.4, 128.6, 136.0, 141.8, 183.0; MS (CI, CH$_4$): m/z (rel. int.) 259 (M+1, 100).

Example 28

1'-Cyclobutylspiro[indoline-3,3'-piperidin]-2-one Hydrochloride

The compound was prepared according to PROCEDURE 1, Method A by reaction with spiro[indoline-3,3'-piperidin]-2-one and cyclobutanone (5 equivalents). $^{13}$C NMR of the HCl-salt (CD$_3$OD): δ 14.4, 19.4, 26.1, 26.9, 31.2, 46.1, 50.4, 53.9, 61.6, 111.5, 123.9, 124.6, 130.4, 131.3, 142.6, 182.2; MS (CI, CH$_4$): m/z (rel. int.) 257 (M+1, 100).

Example 29

1'-Methoxyethylspiro[indoline-3,3'-piperidin]-2-one Hydrochloride

The compound was prepared according to PROCEDURE 1, Method B by reaction with spiro[indoline-3,3'-piperidin]-2-one and 2-chloroethyl methylether (1.2 equivalents) and potassium iodide (catalytic amount). EtOAc was used for extraction. Yield: 74% $^{13}$C NMR (CDCl$_3$): δ 21.8, 31.8, 48.8, 54.2, 58.0, 58.8, 59.2, 70.8, 109.8, 122.0, 126.4, 127.6, 134.8, 140.2, 182.0. The HCl salt was prepared. MS (TSP): m/z (rel. int.) 262/261 (M$^+$, 16/100).

Example 30

1'-Methylthioethylspiro[indoline-3,3'-piperidin]-2-one Hydrochloride

The compound was prepared according to PROCEDURE 1, Method B by reaction with spiro[indoline-3,3'-piperidin]-2-one, 2-chloroethyl methylsulfide (1.2 equivalents) and potassium iodide (catalytic amount). $^{13}$C NMR (CDCl$_3$): δ 15.9, 21.7, 31.8, 31.9, 48.9, 53.3, 58.0, 58.8, 109.8, 122.1, 126.6, 127.7, 134.6, 140.2, 181.9.

The HCl salt was prepared. MS (EI, 70 eV): m/z (rel. int.) 278/277 (M$^+$, 16/100).

Example 31

1'-Methoxypropylspiro[indoline-3,3'-piperidin]-2-one Hydrochloride

The compound was prepared according to PROCEDURE 1, Method B by reaction with spiro[indoline-3,3'-piperidin]-2-one, 3-chloropropyl methyl ether (1.2 equivalents) and potassium iodide (catalytic amount). $^{13}$C NMR (CDCl$_3$): δ 21.8, 27.3, 32.0, 48.8, 53.8, 55.4, 58.8, 58.9, 71.1, 109.6, 122.0, 126.6, 127.7, 134.8, 140.0, 181.4.

The HCl salt was prepared. MS (TSP): m/z (rel. int.) 276/275 (M$^+$, 15/100).

Example 32

(S)-1'-(3-Fluoropropyl)spiro[indoline-3,3'-piperidin]-2-one Hydrochloride

The racemic compound was prepared according to PROCEDURE 1, Method B by reaction of spiro[indoline-3,3'-piperidin]-2-one with 1-bromo-3-fluoropropane (1.0 equivalent). EtOAc was used for extraction. Yield: 69%. $^{13}$C NMR (CDCl$_3$): δ 21.8, 28.0 (d, J$_F$=20 Hz), 31.8, 48.9, 53.9, 54.3 (d, J$_F$=5 Hz), 58.7, 81.7, 83.3, 110.0, 122.0, 126.2, 127.7, 134.7, 140.3, 182.1. The racemate was separated on the Kirasil TBB column and the HCl salt was prepared.

Example 33

(S)-(+)-1'-Propylspiro[indoline-3,3'-piperidin]-2-one

1'-Propyl-1H-spiro[indole-3,3'-piperidin]-2-one (2.9 g, 11.9 mmol) and di-p-toluoyl-L-tartraric acid (4.6 g, 11.9 mmol) were dissolved in ethanol (50 ml) at 40–50° C. Water was added in small portions (totally 50 ml) at the same temperature leaving a clear solution which was slowly cooled to 5° C. The crystals (3.53 g) were collected the next day. A second crystallisation was carried out in a similar manner using the same volume of solvents yielding pure (S)-1'-propylspiro[indole-3,3'-piperidinium]-2-one di-p-toluoyl-L-tartrate (3.2 g) which was converted to the corresponding amine by a treatment with an excess of aqueous sodium bicarbonate. The amine was extracted into ethyl acetate, the extracts were dried over sodium sulfate and concentrated in vacuum. The residue was dissolved in acetonitrile and treated with a 1.5 fold molar excess of hydrochloric acid.

Removal of the volatiles in vacuum and coevaporation with acetonitrile yielded (S)-1'-propylspiro[indole-3,3'-piperidinium]-2-one hydrochloride (113 g, 78%), [α]$_D^{20}$ +91.9° (c 1.00, H$_2$O). The absolute configuration was established by X-ray crystallography of the di-p-toluoyl-L-tartrate.

Example 34

(R)-(−)-1'-Propylspiro[indoline-3,3'-piperidin]-2-one

The mother liquid from the first crystallisation in the previous EXAMPLE, consisting mostly of the other diastereomeric salt was treated with NaHCO$_3$/ethyl acetate to leave the levorotatory amine. This was treated with 1 mol. eq. of di-p-toluoyl-D-tartraric acid and the salt was crystallised from 50% aqueous ethanol. A similar further treatment as in EXAMPLE 27 yielded (R)-1'-propylspiro[indole-3,3'-piperidinium]-2-one hydrochloride (1.09 g, 75%), [α]$_D^{20}$ −91° (c 1.00, H$_2$O).

Example 35

Spiro[indoline-3,3'-perhydroazepin]-2-one

STEP A. N-Benzyl-4-(3-indolyl)-butanamine. Lithium aluminum hydride (4.8 g) was added to a solution of N-benzyl-3-indolebutanamide (18.73 g) in dry THF (200 mL) at nitrogen atmosphere and at 0° C. After stirring at reflux for 15 h and work-up with sodium hydroxide the title compound was obtained as pale yellow crystals (16.4 g).

STEP B. 3-(4-(Benzylamino)-butyl)-indolin-2-one. Conc hydrochloric acid (90 mL) was added to a solution of the compound from the previous step in DMSO (38 mL) and MeOH (8 mL). After stirring for 30 min at 0° C. and 30 min at room temperature the mixture was poured onto ice followed by extractive work-up. The title compound was obtained as a crude orange oil (16.2 g).

STEP C. 1'-Benzylspiro[indoline-3,3'-perhydroazepin]-2-one. A solution of the compound from the previous step (15.5 g) was cyclised via a Mannich reaction following the procedure described in *J Med Chem* 1976, 19, 892. Evaporation, extractive work-up nd purification on silica gave the title compound as a yellow oil (2.4 g).

STEP D. Spiro[indoline-3,3'-perhydroazepin]-2-one hydrochloride. The compound from the previous step was hydrogenated in acetic acid over 10% Pd/C at 40 psi H, for 48 h. Evaporation and extractive work-up gave the title compound as a yellow solid (1.51 g). MS (TSP+) m/z: 217 (M+H$^+$, 100) which was converted to the title compound.

Example 36

1'-Propylspiro[4-azaindoline-3,3'-piperidin]-2-one

STEP A. tert-Butyl 3-[(2-bromo-3-pyridyl)carbamoyl]-1,2,5,6-tetrahydropyridine-1-carboxylate. 2-Bromo-3-pyridineamine (3.0 g, 17.3 mmol) and 1,2,5,6-tetrahydro-1,3-pyridinedicarboxylic acid 1-tert-butyl ester 3-methyl ester (5.05 g, 20.8 mmol) were dissolved in DCM (80 ml). To the solution trimethylaluminium (26 mmol, 2M solution) was slowly added at 0° C. The mixture was refluxed overnight. Work-up and purification on silica gel using 60% ethyl acetate in heptane as an eluent gave 5.65 g (85%) of the title compound.

STEP B. tert-Butyl 3-[N-(2-bromo-3-pyridyl)-N-(tert-butoxycarbonyl)carbamoyl]-1,2,5,6-tetrahydropyridine-1-carboxylate. The compound from STEP A was dissolved in DCM and di-tert-butyl-dicarbonate (3.85 g, 17.6 mmol) was added followed by triethylamine (2.51 ml, 18.0 mmol) and dimethylaminopyridine (0.17 g, 1.4 mmol). After stirring the mixture for 1 h at room temperature methanol was added and the volatiles were removed in vacuum. Purification of the product on a column packed with silica gel using 40% ethyl acetate in heptane as an eluent afforded 6.74 g, (95%) of the title compound.

STEP C. Di-t-butyl 2-oxo-1,1'-spiro[4-azaindoline-3,3'-(1,2,3,6-tetrahydropyridin)]-1,1'-dicarboxylate. The compound from STEP B was dissolved in acetonitrile (80 ml), palladium acetate (0.37 g, 1.67 mmol) and triphenylphosphine (1.0 g, 3.8 mmol) were added and finally triethylamine (2.9 ml, 20.8 mmol). The mixture was refluxed under nitrogen for 2.5 hours. Work-up gave the title compound (4.13 g, 74%).

STEP D. Di-t-butyl 2-oxo-1,1'-spiro[4-azaindoline-3,3'-piperidin]-1,1'-dicarboxylate. The compound from STEP C was hydrogenated in methanol over 10% Pd/C at 50 psi H, for 3 h. Purification on a column packed with silica gel using 60% ethyl acetate in heptane as an eluent gave the title compound (82%).

STEP E. 1'-Propylspiro[4-azaindoline-3,3'-piperidin]-2-one. The compound from STEP D was deprotected using a mixture of 36% hydrochloric acid, methanol and dioxane (1:1:5 volume per cent) at room temperature for 10 h. The volatiles were removed and the crude spiro[4-aza-indole-3,3'-piperidin]-2-one was alkylated according to PROCEDURE 1, Method A. The product was purified on a column with silica gel using 10–20% methanol in ethyl acetate as an eluent to give the title compound (57%). $^{13}$C NMR, δ ppm: 12.9, 20.6, 22.0, 31.0, 49.0, 55.2, 58.1, 62.0, 117.3, 123.4, 136.6, 143.6, 155.4, 181.7.

Example 37

1'-Butylspiro[4-azaindoline-3,3'-piperidin]-2-one

The title compound was synthesised according to the procedure described in EXAMPLE 29 using butanal. $^{13}$C NMR, δ ppm: 15.1, 21.8, 22.0, 29.6, 31.0, 49.0, 55.3, 58.2, 60.0, 117.2, 123.4, 136.6, 143.7, 155.4, 181.7.

Example 38

1'-s-Butylspiro[4-aza-indoline-3,3'-piperidin]-2-one was synthesised according to EXAMPLE 30 using sec-butanal. $^{13}$C NMR, δ ppm: 21.6, 21.9, 22.0, 26.3, 30.9, 49.1, 55.8, 58.4, 67.8, 117.2, 123.4, 136.5, 143.6, 155.4, 181.7.

Example 39

1'-Propyl-5-chlorospiro[7-aza-indoline-3,3'-piperidin]-2-one

STEP A. 3-Bromo-5-chloro-2-pyridineamine. To 5-chloro-2-pyridineamine (3 g, 23.3 mmol) dissolved in acetic acid (40 ml) a solution of bromine (1.29 ml, 25 mmol) in acetic acid was added dropwise at 10° C. The mixture was stirred for 2 h at room temperature and then concentrated. Work-up and purification on a column packed with silica gel using 40% ethyl acetate in heptane as an eluent yielded the title compound as a colourless powder (3.58 g, 74%).

STEP B. t-Butyl 3-[N-(3-bromo-5-chloro-2-pyridyl)-N-(tert-butoxycarbonyl)carbamoyl]-1,2,5,6-tetrahydropyridine-1-carboxylate. The compound from STEP A was treated in a similar manner as was described in EXAMPLE 29, STEPS A and B affording the title compound in good yield.

STEP C. Di-t-butyl 5-chloro-2-oxo-1,1'-spiro[7-azaindoline-3,3'-piperidin]-1,1'-dicarboxylate. The previous amide was cyclized as described in EXAMPLE 29, STEP C and the resulting product was hydrogenated in methanol under 50 psi H$_2$ over 10% Pd/C for 20 hours to give the title compound after chromatografic separation on silica gel. The dechlorinated compound was also obtained in 40% yield.

STEP D. 5-Chloro-spiro[7-azaindoline-3,3'-piperidin]-2-one. The cyclized product from the previous step was deprotected as described in EXAMPLE 29.

STEP E. 1'-Propyl-5-chloro-spiro[7-azaindoline-3,3'-piperidin]-2-one. The compound from the previous step was converted to the title compound as described in EXAMPLE 29. $^{13}$C NMR, δ ppm: 12.8, 21.0, 22.8, 32.3, 49.9, 54.5, 59.3, 61.4, 118.6, 119.3, 135.2, 146.7, 156.7, 181.1.

Example 40

1'-Propylspiro[7-azaindoline-3,3'-piperidin]-2-one

The dechlorinated product from EXAMPLE 33, Step C, was deprotected and alkylated as described in the previous exampel. $^{13}$C NMR, δ ppm: 12.7, 20.8, 22.7, 32.2, 50.3, 54.1, 9.3, 61.4, 123.3, 127.0, 135.8, 145.4, 154.3, 180.4.

Example 41

1'-Propyl-6-methylspiro[7-azaindoline-3,3'-piperidin]-2-one

STEP A. 2-Amino-6-methylpyrid-3-yl trifluoromethane-sulfonate. To a stirred suspension of 2-amino-6-methylpyridin-3-ol (2g) in DCM (50 ml) containing triethy-lamine (2.2 g), trifluoromethanesulfonic anhydride (5.3 g)

was added under N₂ at −78° C. After the mixture became homogeneous, it was allowed to warm to −20° C. and then quenched with aqueous NaHCO₃. Work-up by extraction into chloroform purification on silica gel using 40% ethyl acetate in heptane as an eluent afforded the title compound (86%).

STEP B. 4-(6-Methyl-3-trifluoromethanesulfonyloxy-pyrid-2-ylcarbamoyl)-3,6-dihydro-2H-pyridine-1-carboxylic acid t-butyl ester. The compound from STEP A was treated in a similar manner as was described in EXAMPLE 29, STEP A affording the title compound in 42% yield.

STEP C. t-Butyl 6-methyl-2-oxo-spiro[7-azaindoline-3,3'-(1,2,3,6-tetrahydropyridin)]-1'-carboxylate. The compound from STEP B was treated in a similar manner as was described in EXAMPLE 29, STEP C affording the title compound in 76% yield.

STEP D. t-Butyl 6-methyl-2-oxo-spiro[7-azaindoline-3,3'-piperidin]-1'-carboxylate. The compound from STEP C was treated in a similar manner as was described in EXAMPLE 29, STEP D affording the title compound in 85% yield.

STEP E. 6-Methyl-1'-propylspiro[7-azaindoline-3,3'-piperidin]-2-one dihydrochloride. The compound from STEP D was treated in a similar manner as was described in EXAMPLE 29, STEP E affording the title compound in 66% yield. $^{13}$C NMR, δ ppm: 12.8, 21.0, 22.9, 24.2, 32.4, 49.7, 54.7, 59.6, 61.4, 117.5, 127.0, 135.4, 156.4, 156.9, 181.5. It was converted to the dihydrochloride by treatment with HCl in ethanol and evaporation of solvents.

Example 42

1'-Propylspiro[isoindoline-3,3'-piperidin]-1-one Hydrochloride

STEP A. 2-Bromo-N-(3-pyridyl)benzamide. To a solution of 2-bromobenzoylchloride (11.6 g) in dry pyridine (50 ml) at rt., 3-aminopyridine (5.0 g) dissolved in dry pyridine was added. After stirring for 12 hours and extractive work-up 7.77 g of the title product was obtained as white crystals. MS(ESP+) m/z: 279 (M+H⁺, 98), 277 (M+H⁺, 100).

STEP B. 2-Bromo-N-(1-propyl-1,2,5,6-tetrahydropyridin-3-yl)benzamide. To a stirred solution of the compound from Step A (6.0 g) in dry toluene (100 ml) propylbromide (13.0 g) was added. The reaction mixture was stirred at 80° C. for 16 hours. The precipitated oil was dissolved in MeOH (100 ml) and sodium borohydride (6.0 g) was added slowly at rt. After 3 hours of reaction time, work-up and chromatography on silica gel with ethyl acetate/n-heptane as the eluent 6.65 g of the title product was obtained as an oil. MS(TSP+) m/z: 325 (M+H⁺, 92), 323 (M+H⁺, 100).

STEP C. 2-Iodo-N-(1-benzyl-1,2,5,6-tetrahydropyridin-3-yl)benzamide. To a stirred solution of 2-iodo-N-pyridin-3-ylbenzamide (8.32 g) in dry toluene (200 ml) was added benzyl bromide (5.1 g). The reaction mixture was stirred at 100° C. for 16 hours. The solvent was decanted from the precipitated crystals which were dissolved in MeOH (150 ml) and the treated with sodium borohydride to give 7.9 g of the title compound as white-yellow crystals. MS(TSP+) m/z: 419 (M+H⁺, 100).

STEP D. 1'-Propylspiro[isoindoline-3,3'-piperidin]-one hydrochloride. The compound from STEP B (6.60 g) was cyclised according to the general Heck procedure described in EXAMPLE 1 to give an oil which was chromatographed on silica gel with ethyl acetate/n-heptane as the eluent to give 830 mg 1'-propylspiro-[isoindoline-3,3'-1,2,3,6-tetrahydropyridin]-1-one as an oil. This compound was hydrogenated as described in EXAMPLE 1 yielding the free base of the title compound as white crystals. The title compound was also prepared from cyclization of the STEP C compound followed by hydrogenation-debenzylation plus propylation. $^{13}$C NMR (CDCl₃): δ 169.44, 150.10, 131.77, 131.58, 128.51, 124.14, 121.56, 62.74, 60.87, 60.26, 53.24, 34.88, 23.34, 19.00. 11.82; MS(TSP+) m/z: 245 (M+H⁺, 100); MS(CI, NH₃): 245 (M+H⁺, 100), 180 (3). MP: 110–112°.

The title compound was prepared by treating it with HCl in Et2O. Anal. Calcd for C15H21ClN2O: C, 64.13; H, 7.53; N 10.01 Found: C, 64.25; H, 7.6; N, 10.0.

Example 43

Spiro[3,4-dihydro-1H-quinoline-3,3'-piperidin]-2-one Hydrochloride

STEP A. 1-t-Butyl 3-ethyl 3-(2-nitrobenzyl)-1,3-piperidinedicarboxylate. To a solution of ethyl 1-t-butyloxycarbonyl-3-piperidinecarboxylate (1.5 g) in THF (10 ml) at −78° C. was added lithium hexamethyldisilazide (8.74 ml of a 1M solution in THF). A solution of 2-nitrobenzyl bromide (1.5 g) in THF (5 ml) was added dropwise at −78° C. and the reaction mixture was allowed to reach room temperature. Work-up and chromatography on silica gel with ethyl acetate/petroleum benzine 5:1 as eluent gave 1.3 g of the title compound.

STEP B. 1'-t-Butyl spiro[3,4-dihydro-1H-quinoline-3,3'-piperidin]-2-one-1-carboxylate. To a solution of 1-t-butyl 3-ethyl 3-(2-nitrobenzyl)-1,3-piperidinedicarboxylate (1.2 g) in methanol (25 ml) 10% Pd/C (0.3 g) was added and the mixture was hydrogenated at 30 psi for 2 h. The mixture was filtered and concentrated to yield 0.95 g of the title compound.

STEP C. Spiro[3,4-dihydro-1H-quinoline-3,3'-piperidin]-2-one hydrochloride. The compound (0.90 g) from STEP B was debocylated in ethyl acetate HCl-diethyl ether and the deprotected amine was precipitated as the hydrochloride salt. $^{13}$C NMR (CD₃OD, 400 MHz): δ 20.24, 29.95, 37.14, 38.83, 45.01, 50.28, 116.26, 122.08, 124.74, 129.00, 129.83, 137.42, 175.17.

Example 44

1'-Propylspiro[3,4-dihydro-1H-quinoline-3,3'-piperidin]-2-one Hydrochloride

Spiro[3,4-dihydro-(1H)-quinoline-3,3'-piperidin]-2-one (0.55 g) was propylated according to the general PROCEDURE 1, Method A. The crude product was purified by flash chromatography on silica gel with DCM/methanol 9:1 as eluent to give 0.44 g of the title compound as the free base. $^{13}$C NMR (CDCl₃, 400MHz): δ 11.74, 19.85, 21.18, 29.12, 33.28, 40.82, 54.47, 57.34, 60.51, 114.67, 122.90, 123.03, 127.17, 128.59, 136.48, 175.64. The product was converted to the hydrochloride by dissolving the base in diethyl ether and precipitate with HCl in Et₂O.

Example 45

1'-Isopropylspiro[indoline-3,3'-piperidine] hydrochloride

To a solution of 1'-isopropylspiro[indoline-3,3'-piperidin]-2-one (0.2 g) in THF (10 ml) borane-dimethyl sulfide complex in THF (2 M solution, 0.90 ml) was added.

The reaction mixture was refluxed for 1 h. The solvent was evaporated in vacuo and the residue was refluxed with one equivalent of HCl (g) in ethanol for 30 minutes. After work-up the residue was purified by flash chromatography on silica gel with ethyl acetate as eluent to yield 0.12 g of the base. $^{13}$C NMR (CDCl$_3$, 400 MHz): δ 16.3, 19.6, 23.7, 35.1, 46.2, 50.2, 54.9, 57.2, 57.3, 109.7, 118.2, 123.2, 128.0, 135.9, 151.8. It was converted to the hydrochloride with HCl in ether.

Example 46

1'-Methylspiro[2,3-dihydrobenzofuran-3,3'-piperidine]hydrochloride

STEP A. 2-Iodophenyl (1-methyl-1,2,5,6-tetrahydro-3-pyridinyl)methyl ether. To an ice-cooled stirred solution of triphenylphosphine (1.54 g) and diethyl azodicarboxylate (0.92 ml) in THF (20 ml) 2-iodophenol (1.27 g) and (1-methyl-1,2,5,6-tetrahydro-3-pyridyl)methanol (0.5 g) were added. The mixture was stirred for 72 h at room temperature. The solvent was evaporated and the residue was purified by chromatography on silica gel with first ethyl acetate and then 10% methanol in DCM as eluent to yield 0.98 g of the title compound.

STEP B. 1'-Methylspiro[2,3-dihydrobenzofuran-3,3'-(1,2,3,6-tetrahydropyridin)]. The previous compound (0.42 g) was cyclized following the procedure in EXAMPLE 1 using tri-o-tolylphosphine to yield 0.2 g of the title compound.

STEP C. 1'-Methylspiro[2,3-dihydrobenzofuran-3,3'-piperidine]hydrochloride. To a solution of the previous compound (0.2 g) in acetic acid (10 ml) 10% Pd/C (0.1 g) was added and the mixture was hydrogenated in a Parr apparatus at 50 psi for 6 h. The residue after filtering and evaporation of solvents gave 0.2 g of the title compound. 13C NMR (CDCl$_3$, 400 MHz): δ 22.9, 34.1, 46.1, 46.6, 55.5, 65.0, 81.0, 109.6, 120.1, 123.1, 128.5, 133.9, 158.5. It was converted to the hydrochloride.

Example 47

1'-Propylspiro[2,3-dihydrobenzofuran-3,3'-piperidine]hydrochloride

STEP A. Spiro[2,3-dihydrobenzofuran-3,3'-(1,2,3,6-tetrahydropyridine)]. To a stirred solution of the product from EXAMPLE (0.32 g) in 1,2-dichloroethane (20 ml) 1-chloroethyl chloroformate (0.46 g) was added and the mixture was refluxed for 36 h. After concentration methanol (10 ml) was added and the mixture was refluxed for 4 h. Concentration gave 0.3 g of the product.

STEP B. 1'-Propylspiro[2,3-dihydrobenzofuran-3,3'-(1,2,3,6-tetrahydropiperidine)].

The previous compound was propylated according to PROCEDURE 1, METHOD B giving the title compound in 60% yield.

STEP C. 1'-Propylspiro[2,3-dihydrobenzofuran-3,3'-piperidine]hydrochloride. The previous compound was hydrogenated at 50 psi for 6 h over Pd/C. Work-up yielded the title compound. 13C NMR (CDCl$_3$): δ 12.1, 20.2, 22.8, 34.8, 46.2, 54.1, 60.5, 63.0, 81.8, 109.9, 120.3, 123.2, 128.6, 133.9, 159.5. It was converted to the hydrochloride.

Example 48

Spiro[3,4-dihydro-]H-quinoline-4,3'-piperidin]-2-one Hydrochloride

STEP A. N-(2-Iodophenyl)-2-(4-pyridinyl)acetamide. A solution of 3-pyridylacetic acid to (2.0 g) and triethylamine (2.0 mL) in dry THF (20 mL) was treated at −10° C. with isobutyl chloroformate (2.0 mL). After 10 minutes at −10° C., a solution of 2-iodo-aniline (3.6 g) in THF (10 mL) was added. The reaction mixture was allowed to stir while slowly warming to room temperature. The solvent was evaporated, and the residue was partitioned between ethyl acetate and saturated NaHCO$_3$ solution. The organic layer was dried over MgSO$_4$, filtered, the solvent was evaporated and the residual oil was purified by flash chromatography to yield 1.0 g of the title product. MS (TSP+) m/z [M+H]$^+$: 339.

STEP B. 2-(1-Benzyl-1,2,3,6-tetrahydro-4-pyridinyl)-N-(2-iodophenyl)acetamide. Benzyl bromide (1.0 g) was added to a solution of N-(2-iodophenyl)-2-(4-pyridinyl)acetamide (1.0 g) in acetone. The mixture was stirred at reflux over night. The resulting viscous oil was decanted and used without further purification. To a stirred solution of the pyridinium salt in methanol (20 mL) was added portionwise NaBH$_4$ (0.14 g) at 0° C. during 1 hour. On completion of the addition, the resulting mixture was allowed to warm to room temperature and stirred overnight. Water was added carefully and the resulting mixture was concentrated in vacuo. The residue was extracted twice with ethyl acetate. The organic layer was dried over MgSO$_4$, filtered, the solvent was evaporated and the residual oil was purified by flash chromatography to yield 1.0 g of the title product. MS (TSP+) m/z [M+H]$^+$: 433.

STEP C. 1'-Benzylspiro[3,4-dihydro-1H-quinoline-4,3'-1,2,3,6-tetrahydropyridin]-2-one. The product from STEP B (0.7 g) was dissolved in acetonitrile (20 mL) and triethylamine (0.50 mL) under N$_2$-atmosphere. After 0.5 h tri-o-tolylphosphine (90 mg) and palladium acetate (36 mg) were added in one portion. The mixture was refluxed for 18 hours under N$_2$-atmosphere. The crude product was purified by chromatography on silica gel and eluted with ethyl acetate to give the title compound (0.3 g) as a yellow oil. MS (TSP+) m/z [M+H]$^+$: 305.

STEP D. Spiro[3,4-dihydro-]H-quinoline-4,3'-piperidin]-2-one hydrochloride. The to product from STEP C was hydrogenated in glacial acetic acid (20 mL) using 10% Pd/C and H$_2$ (3.5 atm) for 18 hours. The catalyst was filtered off and the solution was concentrated in vacuo. The residue was dissolved in DCM and saturated NaHCO$_3$ solution and the water layer was extracted three times with DCM. The organic layer was dried over MgSO$_4$, filtered, the solvent was evaporated to yield 0.13 g of the title compound as the free base. $^{13}$ C NMR (CDCl$_3$, 400MHz): δ 22.0, 33.3, 36.2, 38.3, 46.5, 54.3, 116.1, 123.3, 124.9, 127.6, 130.5, 136.6, 171.3. The product was converted to the hydrochloride by dissolving the base in ethyl acetate and precipitate with HCl in Et$_2$O.

Example 49

(S)-(−)-5-Methylspiro[7-azaindoline-3,3'-(1,2,3,6-tetrahydropyridin)]-2-one Dihydrochloride STEP A. t-Butyl 3-(3-bromo-5-methyl-2-pyridylcarbamoyl)-1,2,5,6-tetrahydropyridine-1-carboxylate. It was prepared analogously to EXAMPLE 36, STEP A. in a yield of 53%.

STEP B. t-Butyl 3-[N-(3-bromo-5-methyl-2-pyridyl)-N-(tert-butoxycarbonyl)carbamoyl]-1,2,5,6-tetrahydropyridine-1-carboxylate. The compound from STEP A was converted to the semisolid title compound in a yield of 50% as described in EXAMPLE 36, STEP B.

STEP C. Di-t-butyl 5-methyl-2-oxo-1,1'-spiro[7-azaindoline-3,3'-(1,2,3,6-tetrahydropyridin)]-1,1'-dicarboxylate.

The compound from STEP B was treated as described in EXAMPLE 36, STEP C to give the title compound in 80% yield.

STEP D. t-Butyl 5-methyl-2-oxo-1,1'-spiro[7-azaindoline-3,3'-(1,2,3,6-tetrahydropyridin)]-1'-carboxylate. The compound from STEP C was treated in methanol at reflux with 10 equivalents of ammonium acetate for 2 h. The residue after evaporation of solvent was purified by SGC (EtOAc:isohexanes 1:1 to pure EtOAc) to give the title compound as a white solid. Due to the presence of rotamers it was difficult to obtain good NMR spectra.

STEP E. (S)-(+)-t-Butyl 5-methyl-2-oxo-1,1'-spiro[7-azaindoline-3,3'-(1,2,3,6-tetrahydropyridin)]-1'-carboxylate. The compound from STEP D was chromatographically resolved on a Kirasil TBB column using heptane/2-PrOH 9:1 as an eluent and recycling the eluate twice.

STEP F. (S)-(−)-5-Methylspiro[7-azaindoline-3,3'-(1,2,3,6-pyridin)]-2-one dihydrochloride. The compound from STEP E, second peak, was deprotected using 0.5 M HCl in methanol-ether at room temperature for 15 h. Evaporation of solvents gave the title compound in quantitative yield. It is tentatively assigned the S configuration based on its elution pattern on the chiral column. MS (TSP+) m/z [M+H]$^+$: 216. $[\alpha]_{589}^{22}$ −9 36° (c 1.0, MeOH).

Example 50

(R)-(+)-5-Methylspiro[7-azaindoline-3,3'-(1,2,3,6-tetrahydropyridin)]-2-one Dihydrochloride The material from STEP E, first peak, was deprotected similarly. 13C-NMR (d4-MeOH): 177.6, 152.5, 143.0, 135.6, 131.7, 129.8, 127.4, 123.7, 47.7, 45.6, 42.2, 17.9 ppm. $[\alpha]_{589}^{22}$ +39° (c 1.04, MeOH).

Example 51

(S)-5,6-Dimethylspiro[7-azaindoline-3,3'-(1,2,3,6-tetrahydropyridin)]-2-one Hydrochloride STEP A. t-Butyl 3-(3-bromo-5,6-dimethyl-2-pyridylcarbamoyl)-1,2,5,6-tetrahydropyridine-1-carboxylate. It was prepared analogously to EXAMPLE 36, STEP A starting from 3-bromo-5,6-dimethyl-2-pyridineamine (J. Heterocycl. Chem. 1994, 31, 1641–5) in a yield of 57% after SGC (EtOAc: heptane 1:1→4:1). MS (TSP+) m/z [M+1]$^+$: 410 and 412.

STEP B. t-Butyl 3-[N-(3-bromo-5,6-dimethyl-2-pyridyl)-N-(tert-butoxycarbonyl)carbamoyl]-1,2,5,6-tetrahydropyridine-1-carboxylate. The compound from STEP A was converted to the crude title compound in a yield of 100% as described in EXAMPLE 36, STEP B. MS (TSP+) m/z [M-Boc+1]$^+$410 and 412.

STEP C. Di-t-butyl 5,6-dimethyl-2-oxo-1,1'-spiro[7-azaindoline-3,3'-(1,2,3,6-tetrahydropyridin)]-1,1'-dicarboxylate. The compound from STEP B was treated as described in EXAMPLE 36, STEP C to give the title compound in 70% yield.

STEP D. t-Butyl 5,6-dimethyl-2-oxo-1,1'-spiro[7-azaindoline-3,3'-(1,2,3,6-tetrahydropyridin)]-1'-carboxylate. The compound from STEP C was treated in methanol at reflux with 10 equivalents of ammonium acetate for 2 h. The residue after evaporation of solvent was purified by SGC (EtOAc:heptane 1:1) to give the title compound as a white solid. Due to the presence of rotamers it was difficult to obtain good NMR spectra. MS (TSP+) m/z [M+1]$^+$330.

STEP E. (S)-t-Butyl 5,6-dimethyl-2-oxo-1,1'-spiro[7-azaindoline-3,3'-(1,2,3,6-tetrahydropyridin)]-1'-carboxylate. The compound from STEP D was chromatographically resolved on a Kirasil TBB column using heptane/2-PrOH 95:5 as an eluent and recycling the eluate twice.

STEP F. (S)-5,6-Dimethylspiro[7-azaindoline-3,3'-(1,2,3,6-tetrahydropyridin)]-2-one dihydrochloride. The compound from STEP E, second peak (190 mg), was deprotected using 0.5 M HCl in methanol-ether at room temperature for 15 h. Evaporation of solvents gave the title compound in quantitative yield. It is tentatively assigned the S configuration based on its elution pattern on the chiral column. MS (TSP+) m/z [M+H]$^+$: 230. $^1$H-NMR (d$_4$-MeOH): 7.80 (s, 1H), 6.11 (d, 1H), 5.54 (d, 1H), 3.75 (m, 2H), 3.52 (dd, 2H), 2.4 (s, 3H), 218 (s, 2H).

The following EXAMPLES 52–81 were prepared analogously to EXAMPLE 49 and 51 starting with an aniline or other aromatic amine. The mono-Boc protected intermediates were separated using a Kirasil TBB (PROCEDURE 2) or Chiralpak AD column. All resolved compounds obtained from the last eluting peak on the Kirasil TBB column are assumed to have the S configuration, and vice versa.

Example 52

(S)-5-Chlorospiro [7-azaindoline-3,3'-(1,2,3,6-tetrahydropyridin)]-2-one Dihydrochloride $^{13}$C-NMR (D$_2$O), δ: 42.1, 45.5, 48.0, 123.7, 126.2, 126.7, 127.7, 135.2, 146.4, 154.9, 180.0 ppm.

Example 53

(R)-5-Chlorospiro[7-azaindoline-3,3'-(1,2,3,6-tetrahydropyridin)]-2-one Dihydrochloride MS (TSP+) m/z [M+H]$^+$: 235.

Example 54

(R)-6-Methylspiro[7-azaindoline-3,3'-(1,2,3,6-tetrahydropyridin)]-2-one Dihydrochloride $^{13}$C-NMR (D$_2$O): δ 20.3, 42.0, 45.2, 47.3, 120.5, 123.1, 124.7, 127.3, 140.2, 151.7, 153.4, 179.3 ppm.

Example 55

(S)-6-Methylspiro[7-azaindoline-3,3'-(1,2,3,6-tetrahydropyridin)]-2-one Dihydrochloride MS (TSP+) m/z [M+H]$^+$: 216.

Example 56

(S)-7-Fluorospiro[indoline-3,3'-(1,2,3,6-tetrahydropyridin)]-2-one Hydrochloride $^{13}$C-NMR (d$_4$-MeOH): 179.7, 149.9, 147.5, 133.3, 131.0, 130.4, 126.3, 125.9, 125.1, 125.0, 121.16, 121.13, 117.9, 117.7, 109.5, 47.0, 42.6, 30.7 ppm.

Example 57

(R)-7-Fluorospiro[indoline-3,3'-(1,2,3,6-tetrahydropyridin)]-2-one Hydrochloride MS (TSP+) m/z [M+H]$^+$: 219.

Example 58

(S)-4-Methylspiro[indoline-3,3'-(1,2,3,6-tetrahydropyridin)]-2-one Hydrochloride $^{13}$C-NMR (d$_4$-MeOH): 180.1, 143.4, 137.0, 131.0, 127.1, 126.4, 126.3, 125.2, 109.5, 45.6, 42.8, 17.8 ppm.

Example 59

(R)-4-Methylspiro[indoline-3,3'-(1,2,3,6-tetrahydropyridin)]-2-one Hydrochloride MS (TSP+) m/z [M+H]$^+$: 215.

Example 60

(S)-Spiro[indoline-3,3'-(1,2,3,6-tetrahydropyridin)]-2-one Hydrochloride

MS (TSP+) m/z [M+H]$^+$: 201. $^{13}$C-NMR (d$_4$-MeOH): δ 180.0, 141.6, 131.1, 127.1, 125.5, 125.4, 124.3, 117.2, 47.2, 43.0 ppm.

Example 61

(R)-Spiro[indoline-3,3'-(1,2,3,6-tetrahydropyridin)]-2-one Hydrochloride

MS (TSP+) m/z [M+H]$^+$: 201.

Example 62

(R)-5,7-Difluorospiro[indoline-3,3'-(1,2,3,6-tetrahydropyridin)]-2-one Hydrochloride MS (TSP+) m/z [M+H]$^+$: 237.

Example 63

(S)-5,7-Difluorospiro[indoline-3,3'-(1,2,3,6-tetrahydropyridin)]-2-one Hydrochloride MS (TSP+) m/z [M+H]$^+$: 237.

Example 64

(R)-5-Trifluoromethoxyspiro[indoline-3,3'-(1,2,3,6-tetrahydroyridin)]-2-one Hydrochloride $^{13}$C-NMR (d$_4$-MeOH): 179.9, 146.1, 142.4, 132.1, 126.0, 125.9, 124.3, 123.2, 120.7, 119.6, 112.6, 111.8, 46.6, 42.6, 30.7 ppm.

Example 65

(S)-5-Trifluoromethoxyspiro[indoline-3,3'-(1,2,3,6-tetrahydropyridin)]-2-one Hydrochloride MS (TSP+) m/z [M+H]$^+$: 285.

Example 66

(R)-5-Chlorospiro[indoline-3,3'-(1,2,3,6-tetrahydropyridin)]-2-one Hydrochloride MS (TSP+) m/z [M+H]$^+$: 235. $^1$H-NMR (d$_4$-MeOH): 7.4 (m, 1H), 7.37 (d, 1H), 6.97 (d, 1H) 6.22 (d, 1H), 5.65 (d, 1H), 3.90 (m, 1H), 3.60 (m, 1H).

Example 67

(S)-5-Chlorospiro[indoline-3,3'-(1,2,3,6-tetrahydropyridin)]-2-one Hydrochloride MS (TSP+) m/z [M+H]$^+$: 235.

Example 68

(R)-5-Chloro-7-fluorospiro[indoline-3,3'-(1,2,3,6-tetrahydropyridin)]-2-one Hydrochloride MS (TSP+) m/z [M+H]$^+$: 253. $^1$H-NMR (d$_4$-MeOH): 7.3 (m, 2H), 6.2 (m, 1H), 5.7 (m, 1H), 3.9 (m, 1H), 3.6 (m, 1H). Enantiomeric purity 98.0%.

Example 69

(S)-5-Chloro-7-fluorospiro[indoline-3,3'-(1,2,3,6-tetrahydropyridin)]-2-one Hydrochloride MS (TSP+) m/z [M+H]$^+$: 253.

Example 70

(R)-7-Chlorospiro[indoline-3,3'-(1,2,3,6-tetrahydropyridin)]-2-one Hydrochloride MS (TSP+) m/z [M+H]$^+$: 235. $^{13}$C-NMR (d$_4$-MeOH): 180.0, 141.6, 132.5, 131.4, 126.7, 126.1, 125.6, 124.3, 117.2, 47.2, 43.0 ppm.

Example 71

(S)-7-Chlorospiro[indoline-3,3'-(1,2,3,6-tetrahydropyridin)]-2-one Hydrochloride MS (TSP+) m/z [M+H]$^+$: 235.

Example 72

(S)-6-Chlorospiro[indoline-3,3'-(1,2,3,6-tetrahydropyridin)]-2-one Hydrochloride MS (TSP+) m/z [M+H]$^+$: 235. $^{13}$C-NMR (d$_4$-MeOH): 180.4, 145.1, 137.0, 129.4, 127.0, 126.8, 126.0, 124.4, 112.6, 47.1, 43.0 ppm.

Example 73

(S)-5-Methylspiro[indoline-3,3'-(1,2,3,6-tetrahydropyridin)]-2-one Hydrochloride $^{13}$C-NMR (CDCl$_3$) δ 180.2, 140.6, 134.1, 131.2, 130.4, 127.0, 125.9, 125.2, 111.5, 48.0, 47.1, 42.7, 21.1. MS(ESP+) m/z calcd for [M−Cl]$^+$: 215, observed: 215.

Example 74

(S)-5-Fluorospiro[indoline-3,3'-(1,2,3,6-tetrahydropyridin)]-2-one Hydrochloride MS (TSP+) m/z [M+H]$^+$: 219. $^1$H-NMR (d$_4$-MeOH): 7.1, 7.0, and 6.9 (3 m, 3H), 6.18 (d, 1H), 5.57 (d, 1H), 3.85 (dd, 2H), 3.52 (s, 2H).

Example 75

(S)-4-Chlorospiro[indoline-3,3'-(1,2,3,6-tetrahydropyridin)]-2-one Hydrochloride MS (TSP+) m/z [M+H]$^+$: 235.

EXAMPLE 76

(R)-4-Methoxyspiro[indoline-3,3'-(1,2,3,6-tetrahydropyridin)]-2-one Hydrochloride MS (TSP+) m/z [M+H]$^+$: 231. $^{13}$C-NMR (CDCl$_3$) δ 179.7, 157.7, 144.2, 132.6, 126.5, 124.5, 115.8, 107.2, 105.1, 56.3, 48.1, 45.8, 42.7.

Example 77

(R)-6-Methoxyspiro[indoline-3,3'-(1,2,3,6-tetrahydropyridin)]-2-one Hydrochloride MS (TSP+) m/z [M+H]$^+$: 231.

Example 78

(S)-7-Fluoro-5-methylspiro[indoline-3,3'-(1,2,3,6-tetrahydropyridin)]-2-one Hydrochloride MS (TSP+) m/z [M+H]$^+$: 233.

Example 79

5-Fluorospiro[7-azaindoline-3,3'-(1,2,3,6-tetrahydropyridin)]-2-one Hydrochloride MS (TSP+) m/z [M+H]$^+$: 220.

Example 80

(S)-6-Fluorospiro[indoline-3,3'-(1,2,3,6-tetrahydropyridin)]-2-one Hydrochloride MS (TSP+) m/z [M+H]$^+$: 219. $^1$H NMR (CD$_3$OD): δ 7.1 (m, 1H), 6.6 (m, 2H), 6.0 (d, 1H), 5.5 (d, 1H), 3.7 (s, 2H), 3.1 (s, 1H), 1.1 (s, 1H).

Example 81

(S)-5-Methoxyspiro[indoline-3,3'-(1,2,3,6-tetrahydropyridin)]-2-one Hydrochloride MS (TSP+) m/z [M+H]$^+$: 231. $^1$H NMR (CDCl$_3$, 400 MHz) δ 6.9 (d, 1H), 6.8 (dd, 1H), 6.7 (d, 1H), 6.1 (d, 1H), 5.6 (d, 1H), 3.9 (s, 2NH), 3.8 (s, 2H), 3.5 (d, 1H), 3.4 (d, 1H), 3.1 (s, 3H).

Example 82

6H-4,5-Dihydro-2-methylspiro[pyrrolo[2,3-c]pyrazole-4,3'-(1,2,3,6-tetrahydropyridin)]-5-one Hydrochloride The compound is made from commercially available 3-amino-4-bromo-1-methylpyrazole following the general procedure via Heck cyclisation described in Example 49.

Example 83

6H-4,5-Dihydro-2-methylspiro[thieno[2,3-b]pyrrole-4,3'-(1,2,3,6-tetrahydropyridin)]-5-one Hydrochloride The compound is made from known N-Boc-2-amino-4-iodothiophene following the general procedure via Heck cyclisation described in Example 49.

Example 84

5-Chlorospiro[indoline-3,3'-piperidin]-2-one Hydrochloride

The compound from EXAMPLE 65 was hydrogenated over Pd/C at 3 bar in ethanol. MS (TSP+) m/z [M+H]$^+$: 237.

Example 85

Spiro[indoline-3,3'-(1,3,4,7-tetrahydro-2H-azepin)]-2-one Hydrochloride

STEP A. 3-Allyl-3-[allyl(methyl)aminomethyl]-indolin-2-one. Oxindole was acylated with ethyl acetate in the presence of sodium ethoxide as described (Chem. Abstr. 1953, 47, p7488). The crude product (9.16 g; 52.3 mmol) was treated with sodium hydride (56 mmol) in DMF at ice bath temperature for 30 min. Allyl bromide (51 mmol) was added and the reaction mixture left at room temperature overnight. The crude product after workup was purified by SGC (EtOAc/isohexanes 1:2). The acetyl group was removed by treatment with triethylamine/water 1:1 at 65° C. for 12 h and the the 3-allyloxindole thus obtained was treated with an excess of allylmethylamine and one equivalent of paraformaldehyde in acetic acid at 70 for 4 h. The crude material after evaporation of solvents was partioned between DCM and basic water. SGC using EtOAc/isohexanes 1:1 gave a reddish oil of the title product(83%).

STEP B. N'-Methylspiro[indoline-3,3'-(1,3,4,7-tetrahydro-2H-azepin)]-2-one. The product from the previous step (258 mg; 1.0 mmol) was treated with bis(tricyclopentylphosphine)benzylidene-Ru(IV) dichloride (104 mg; 0.14 mmol) in dry toluene under nitrogen at 60° C. for three days. An additional 60 mg of the Ru-catalyst was added and the heating continued overnight. SGC after evaporation of solvents yielded 55 mg (21%) of the title compound.

STEP C. t-Butyl 2-oxospiro[indoline-3,3'-(1,3,4,7-tetrahydro-2H-azepine)]-1'-carboxylate. The spiro compound from STEP B (180 mg) was demethylated by treatment with 1-chloroethyl chloroformate in 1,2-dichloroethane at reflux for 2 h followed after evaporation of excess formiate by heating in methanol-THF-water for 1 h. The secondary amine was bocylated by treatment with (Boc)$_2$O and the product was chromatographed on the Kirasil TBB column using heptane/iPrOH 9:1 as the eluent; two peaks were collected.

STEP D. (S)-Spiro[indoline-3,3'-(1,3,4,7-tetrahydro-2H-azepin)]-2-one Hydrochloride The material from the second peak from STEP C (47 mg) was dissolved in methanol (5 ml) and treated with HCl in ether (1.5 ml) at room temperature overnight. The title compound was obtained upon removal of solvents. MS (TSP+) m/z [M+H]$^+$: 215. $^{13}$C NMR: (CD3OD): 181.0, 142.1, 132.7, 132.2, 130.4, 125.7, 124.8, 123.8, 111.6, 53.8, 47.6, 47.5, 35.4 ppm.

Procedure 1

Exemplified General Methods for Synthesis of Tertiary Amines by Alkylation of a Secondary Amine

METHOD A

To a stirred solution of spiro[indoline-3,3'-piperidin]-2-one and a corresponding aldehyde or ketone (in excess) in methanol, sodiumcyanoborohydride (about 2 eq) was added. The pH was adjusted to about pH 4–6 with acetic acid and the solution was stirred at room temp for about 18–60 h. Concentration and extraction (EtOAc/1–2 M NH$_3$), drying of the combined organic phases and evaporation gave a crude product. Purification by flash column chromatography (SiO$_2$, eluent: toluene/acetonitrile/triethylamine or acetone/isohexane) gave the title compound.

METHOD B

To a stirred solution of a spiro[indoline-3,3'-piperidin]-2-one in acetonitrile or DMF potassium carbonate (1.0–1.4 equivalents) and a corresponding alkyl halide (1.1–1.5 equivalents) was added at 0° C. or room temp. The reaction mixture was stirred at room temp –60° C. for 2–15 h. Concentration and extraction (DCM/water), drying of the combined organic phases and evaporation gave a crude product. Purification by flash column chromatography (SiO$_2$, eluent: acetone/isohexane or toluene/acetonitrile/triethylamine) gave the title compound.

Procedure 2

Examples of Resolving Racemates by Chiral HPLC

The resolution of 1'-isopropylmethylspiro[indoline-3,3'-piperidin]-2-one (861 mg) was performed by chiral HPLC on a Kirasil TBB (50×250 mm) column. Eluent: heptane/1-PrOH/1-BuOH 97:2:1. About 170 mg was loaded on the column each time and the substance was recycled twice on the column; 370 mg of (R)-enantiomer (>99% ee) and 380 mg of the (S)-enantiomer (93% ee) were isolated.

Other tertiary amines could be similarly separated. In most cases it proved possible to check the enantiomeric purity of tertiary as well as secondary amines using chiral liquid chromatography on for example a Chiracel OD column.

It also proved possible to separate several mono-Boc derivatives of secondary amine intermediates on the Kirasil TBB column. One example is described in EXAMPLE 49, STEP E.

BIOLOGICAL TESTS

1. In Vivo Experiments

The compounds of the invention when given by systemic injection to mice or rats, specifically reduce pain behavior in the formalin test. This test is an accepted model of clinical pain in man, involving elements of nociceptor activation, inflammation, peripheral sensitization and central sensitization (A Tjølsen et al. Pain 1992, 51, 5). It can therefore be inferred that the compounds can be used as therapeutic agents to relieve pain of various origins. The compounds of the table "Further most preferred compounds of the invention" exhibit ED 50 doses by subcutaneous administration to mice in the range 0.2–6 μmol/kg. The compounds of formula I also show analgesic activity in the intraarticular FCA (Freund's complete adjuvant) test in the rat, a model of inflammatory pain (Iadarola et al. Brain Research 1988, 455, 205–12) and in the Chung nerve lesion test in the rat, a model for neuropathic pain (Kim and Chung. Pain 1992, 50, 355). The analgesic effects in the animal models are obtained after doses that do not produce tissue concentrations leading to conduction block in nerve fibers. Thus, the analgesic effects can not be explained by the local anesthetic properties of the compounds mentioned in the publication by Komet and Thio. Analgesic efficacy after systemic administration is not a general property of drugs with local anesthetic effects (Scott et al. British Journal of Anaesthesia 1988, 61, 165–8).

What is claimed is:

1. A compound of the formula I

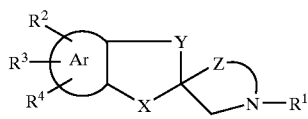

(I)

in racemic form or in the form of an enantiomer, or a pharmaceutically acceptable salt thereof, wherein $R^1$ is
a) H,
b) substituted or unsubstituted $C_1$–$C_6$ alkyl,
c) $C_1$–$C_6$ alkoxy $C_1$–$C_6$ alkyl,
d) $C_1$–$C_6$ alkylthio $C_1$–$C_6$ alkyl,
e) halogenated $C_1$–$C_6$ alkyl,
f) aryl $C_1$–$C_6$ alkyl,
g) $C_1$–$C_6$ alkenyl, or
h) $C_1$–$C_6$cycloalkyl $C_1$–$C_2$ alkyl;

$R^2$ is
a) H,
b) $C_1$–$C_6$ alkyl,
c) $C_2$–$C_4$ alkynyl,
d) halogen,
e) substituted or unsubstituted carbamoyl,
f) substituted or unsubstituted carbamoyloxy,
g) $C_1$–$C_6$ alkylcarbonyl,
h) $C_1$–$C_6$ alkoxycarbonyl,
i) $C_1$–$C_6$ alkylcarbonyloxy,
j) hydroxy-substituted $C_1$–$C_6$ alkyl,
k) cyano,
l) nitro,
m) amino,
n) halogenated $C_1$–$C_6$ alkyl,
o) halogenated $C_1$–$C_6$ alkoxy,
p) halogenated $C_1$–$C_6$ alkylthio,
q) $C_1$–$C_6$ alkylsulfinyl,
r) $C_1$–$C_6$ alkylsulfonyl,
s) $C_1$–$C_4$ alkylsulfinylalkyl,
t) $C_1$–$C_4$ alkylsulfonylalkyl,
u) $C_1$–$C_6$ alkylsulfonylamino,
v) halogenated $C_1$–$C_6$ alkylsulfonylamino,
w) halogenated $C_1$–$C_2$ alkylsulfonyloxy,
x) aminosulfonyl,
y) aminosulfonyloxy,
z) aryl,
aa) arylcarbonyl,
bb) arylsulfinyl,
cc) arylsulfonyl,
dd) $C_1$–$C_6$ alkylcarbonylamino,
ee) $C_1$–$C_6$ alkoxycarbonylamino,
ff) $C_1$–$C_6$ alkyl-thiocarbonyl,
gg) $C_1$–$C_6$ alkoxy-thiocarbonyl,
hh) formyl, or
ii) alkoxysulfonylamino;

$R^3$ is
a) H,
b) $C_1$–$C_6$ alky,
c) halogen,
d) $C_1$–$C_6$ alkoxy,
e) halogenated $C_1$–$C_4$ alkyl,
f) halogenated $C_1$–$C_6$ alkoxy,
g) halogenated $C_1$–$C_6$ alkylthio,
h) $C_1$–$C_4$ aksulfinyl,
i) $C_1$–$C_4$ alkylsulfonyl,
j) $C_1$–$C_4$ alkylsulfinyl $C_1$–$C_6$ alkyl,
k) $C_1$–$C_4$ alkylsulfonyl $C_1$–$C_6$ alkyl,
l) $C_1$–$C_4$ alkylsulfonylamino,
m) halogenated $C_1$–$C_4$ alkylsulfonylamino,
n) aminosulfonyl, or
o) aminosulfonyloxy;

$R^4$ is
a) H,
b) $C_1$–$C_4$ alkyl, or
c) halogen;

$R^2$ and $R^3$ may together with the carbon atoms to which they are attached form a saturated or unsaturated ring, optionally substituted with one or more substituents selected from halogen, $C_1$–$C_6$ alkyl, $C_1$–$C_6$ alkoxy, $CF_3$, OH, cyano, amino, $C_1$–$C_6$ alkyl-NH—, ($C_1$–$C_6$ alkyl)$_2$—N—, CN, $NH_2SO_2$, $NH_2CO$—, or $C_1$–$C_6$ alkyl-CO—;

and wherein any amino moiety in $R^2$–$R^4$ can optionally be substituted with one or two $C_1$–$C_6$ alkyl groups which may be part of a ring, Ar is
a) benzene, or
b) pyridine, X is
a) —NHCO—,
b) —CONH—, or
c) —NH—$SO_2$—;

Y is a single bond; and

Z is —CH=CHCH$_2$ and with the proviso that when R$^1$ is a substituted or unsubstituted C$_1$–C$_6$ alkyl, then R$^2$, R$^3$ and R$^4$ cannot all be hydrogen.

2. The compound of claim 1, wherein

R$^1$ is
- a) H,
- b) C$_1$–C$_4$ alkyl,
- c) C$_1$–C$_4$ alkoxy C$_1$–C$_4$ alkyl,
- d) C$_1$–C$_4$ alkylthio C$_1$–C$_4$ alkyl,
- e) fluorinated C$_1$–C$_4$ alkyl,
- f) aryl C$_1$–C$_4$ alkyl,
- g) C$_1$–C$_4$ alkenyl, or
- h) cyclopropylmethyl;

R$^2$ is
- a) H,
- b) C$_1$–C$_4$ alkyl,
- c) C$_2$–C$_3$ alkynyl,
- d) halogen,
- e) substituted or unsubstituted carbamoyl,
- f) substituted or unsubstituted carbamoyloxy,
- g) C$_1$–C$_3$ alkylcarbonyl,
- h) C$_1$–C$_3$ alkoxycarbonyl,
- i) C$_1$–C$_3$ alkylcarbonyloxy,
- j) hydroxy-substituted C$_1$–C$_3$ alkyl,
- k) cyano,
- l) fluorinated C$_1$–C$_3$ alkoxy,
- m) fluorinated C$_1$–C$_6$ alkylthio,
- n) C$_1$–C$_3$ alkylsulfinyl,
- o) C$_1$–C$_3$ alkyl sulfonyl,
- p) C$_1$–C$_3$ alkylsulfinyl C$_1$–C$_6$ alkyl,
- q) C$_1$–C$_4$ alkylsulfonyl C$_1$–C$_6$ alkyl,
- r) C$_1$–C$_3$ alkylsulfonylamino,
- s) halogenated C$_1$–C$_3$ alkylsulfonylamino,
- t) sulfamoyl,
- u) sulfamoyloxy,
- v) aryl,
- w) arylsulfonyl,
- x) C$_1$–C$_4$ alkylcarbonylamino,
- y) C$_1$–C$_3$ alkoxycarbonylamino,
- z) C$_1$–C$_3$ alkyl-thiocarbonyl, or
- aa) C$_1$–C$_3$ alkoxy-thiocarbonyl;

R$^3$ is
- a) H,
- b) C$_1$–C$_4$ alkyl, or
- c) halogen;

R$^4$ is
- a) H,
- b) C$_1$–C$_4$ alkyl, or
- c) halogen,

R$^2$ and R$^3$ may together with the carbon atoms to which they are attached, form a saturated or unsaturated ring, optionally substituted with one or more substituents selected from halogen, C$_1$–C$_6$ alkyl, C$_1$–C$_6$ alkoxy, CF$_3$, OH, cyano, amino, C$_1$–C$_6$ alkyl-NH—, (C$_1$–C$_6$ alkyl)$_2$N—, CN, NH$_2$SO$_2$, NH$_2$CO—, or C$_1$–C$_6$alkyl-CO—;

and wherein any amino moiety in R$^2$–R$^4$ can optionally be substituted with one or two C$_1$–C$_6$ alkyl groups which may be part of a ring.

3. The compound of either claim 1 or 2, wherein

R$^1$ is
- a) H,
- b) C$_1$–C$_4$ alkyl, or
- c) C$_1$–C$_4$ alkoxy C$_1$–C$_4$ alkyl;

R$^2$ is
- a) H,
- b) C$_1$–C$_4$ alkyl,
- c) halogen,
- d) substituted or unsubstituted carbamoyl,
- e) substituted or unsubstituted carbamoyloxy,
- f) C$_1$–C$_2$ alkylcarbonyl,
- g) C$_1$–C$_3$ alkoxycarbonyl,
- h) cyano,
- i) fluorinated C$_1$–C$_2$ alkoxy,
- j) fluorinated C$_1$–C$_6$ alkylthio,
- k) C$_1$–C$_3$ alkylsulfinyl,
- l) C$_1$–C$_3$ alkylsulfonyl,
- m) C$_1$–C$_2$ alkylsulfonylamino,
- n) C$_1$–C$_3$ alkylcarbonylamino, or
- o) C$_1$–C$_3$ alkoxycarbonylamino;

R$^3$ is
- a) H,
- b) C$_1$–C$_4$ alkyl, or
- c) halogen;

R$^4$ is
- a) H,
- b) C$_1$–C$_4$ alkyl, or
- c) halogen;

R$^2$ and R$^3$ may together with the carbon atoms to which they are attached, form a saturated or unsaturated ring, optionally substituted with one or more substituents selected from halogen, C$_1$–C$_6$ alkyl, C$_1$–C$_6$ alkoxy, CF$_3$, OH, cyano, amino, C$_1$–C$_6$ alkyl-NH—, (C$_1$–C$_6$ alkyl)$_2$—N—, CN, NH$_2$SO$_2$, NH$_2$CO—, or C$_1$–C$_6$ alkyl-CO—;

and wherein any amino moiety in R$^2$–R$^4$ can optionally be substituted with one or two C$_1$–C$_6$ alkyl, groups which may be part of a ring.

4. A compound according to claim 1, wherein

R$^1$ is H;

R$^2$ is
- a) H,
- b) C$_1$–C$_4$ alkyl, or
- c) halogen;

R$^3$ is
- a) H,
- b) C$_1$–C$_4$ alkyl, or
- c) halogen;

R$^4$ is
- a) H,
- b) C$_1$–C$_4$ alkyl, or
- c) halogen.

5. The compound according to claim 4 wherein X is —NHCO—.

6. The compound according to claim 4, wherein Ar is benzene.

7. The compound according to claim 4 wherein Ar is pyridine.

8. A compound or a pharmaceutically acceptable salt thereof, selected from the group consisting of:

(S)-5-chloro-7-fluorospiro[indoline-3,3'-(1,2,3,6-tetrahydropyridin)]-2-one (S)-5-methylspiro[7-azaindoline-3,3'-(1,2,3,6-tetrahydropyridin)]-2-one (S)-5,6-dimethylspiro[7-azaindoline-3,3'-(1,2,3,6-tetrahydropyridin)]-2-one (S)-6-methylspiro[7-azaindoline-3,3'-(1,2,3,6-tetrahydropyridin)]-2-one (S)-5-chlorospiro[7-azaindoline-3,3'-(1,2,3,6-tetrahydropyridin)]-2-one (S)-5,7-difluorospiro[indoline-3,3'-(1,2,3,6-tetrahydropyridin)]-2-one (S)-7-chlorospiro[indoline-3,3'-(1,2,3,6-tetrahydropyridin)]-2-one (S)-7-fluoro-5-methylspiro[indoline-3,3'-(1,2,3,6-tetrahydropyridin)]-2-one (S)-5-methoxyspiro[indoline-3,3'-(1,2,3,6-tetrahydropyridin)]-2-one.

9. The compound (S)-5-chloro-7-fluorospiro[indoline-3,3'-(1,2,3,6-tetrahydropyridin)]-2-one or a therapeutically acceptable salt thereof.

10. The compound (S)-5-methylspiro[7-azaindoline-3,3'-(1,2,3,6-tetrahydropyridin)]-2-one or a therapeutically acceptable salt thereof.

11. The compound (S)-5,6-dimethylspiro[7-azaindoline-3,3'-(1,2,3,6-tetrahydropyridin)]-2-one or a therapeutically acceptable salt thereof.

12. The compound (S)-6-methylspiro[7-azaindoline-3,3'-(1,2,3,6-tetrahydropyridin)]-2-one or a therapeutically acceptable salt thereof.

13. The compound (S)-5-chlorospiro[7-azaindoline-3,3'-(1,2,3,6-tetrahydropyridin)]-2-one or a therapeutically acceptable salt thereof.

14. The compound (S)-5,7-difluorospiro[indoline-3,3'-(1,2,3,6-tetrahydropyridin)]-2-one or a therapeutically acceptable salt thereof.

15. The compound (S)-7-chlorospiro[indoline-3,3'-(1,2,3,6-tetrahydropyridin)]-2-one or a therapeutically acceptable salt thereof.

16. The compound (S)-7-fluoro-5-methylspiro[indoline-3,3'-(1,2,3,6-tetrahydropyridin)]-2-one or a therapeutically acceptable salt thereof.

17. The compound (S)-5-methoxyspiro[indoline-3,3'-(1,2,3,6-tetrahydropyridin)]-2-one or a therapeutically acceptable salt thereof.

18. A pharmaceutical formulation comprising a compound according to claim 1 as an active ingredient together with a pharmaceutically acceptable diluent or carrier.

19. A pharmaceutical formulation comprising a compound according to claim 8 as an active ingredient together with a pharmaceutically acceptable diluent or carrier.

20. A method for the treatment of pain, comprising administering to a mammal in need of such treatment an effective amount of a compound according to any one of claims 1 or 8 to 17.

21. The method of claim 20, wherein said pain is neuropathic pain.

22. The method of claim 20, wherein said compound is administered orally.

23. The method of claim 20, wherein said mammal is a man.

24. A process for the preparation of a compound according to any one of claims 1, or 2 comprising:

a) reacting a compound of formula IV

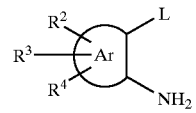

wherein L is a halogen or a trifluoromethylsulonyloxy group, and Ar, $R^2$, $R^3$ and $R^4$ are as defined for Formula I in claims to 1, 2 or 4 to 17, with a compound of Formula II or a corresponding lower alkyl ester

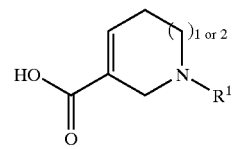

wherein $R^1$ is as defined for Formula I in claims 1, 2 or 4 to 17 or is a nitrogen protecting group, to give a compound of Formula VII

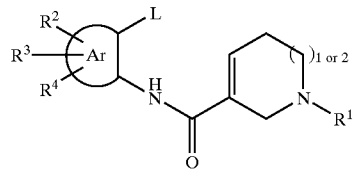

b) cyclizing the compound of Formula VII using a palladium catalyst and optionally removing protecting groups to give said compound.

* * * * *

UNITED STATES PATENT AND TRADEMARK OFFICE
CERTIFICATE OF CORRECTION

PATENT NO.   : 6,774,132 B1
DATED        : August 10, 2004
INVENTOR(S)  : Alf Claesson et al.

It is certified that error appears in the above-identified patent and that said Letters Patent is hereby corrected as shown below:

Title page,
Item [*] Notice, should read:
-- Subject to any disclaimer, the term of this
   patent is extended or adjusted under 35
   U.S.C. 154(b) by 160 days --.

Signed and Sealed this

Twenty-second Day of November, 2005

JON W. DUDAS
*Director of the United States Patent and Trademark Office*